United States Patent
Takamatsu et al.

(10) Patent No.: US 7,473,801 B2
(45) Date of Patent: Jan. 6, 2009

(54) METHOD FOR PURIFICATION OF AMINO ACID

(75) Inventors: Yoshikazu Takamatsu, Kurashiki (JP); Minoru Yamamoto, Kurashiki (JP); Yoshinari Sato, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 11/547,124

(22) PCT Filed: Apr. 6, 2005

(86) PCT No.: PCT/JP2005/006753

§ 371 (c)(1),
(2), (4) Date: Aug. 1, 2007

(87) PCT Pub. No.: WO2005/097734

PCT Pub. Date: Oct. 20, 2005

(65) Prior Publication Data

US 2008/0045746 A1    Feb. 21, 2008

(30) Foreign Application Priority Data

Apr. 7, 2004 (JP) .............................. 2004-113554
Jun. 1, 2004 (JP) .............................. 2004-163593

(51) Int. Cl.
*C07C 227/00* (2006.01)
(52) U.S. Cl. .................................................... 562/554
(58) Field of Classification Search .................. None
See application file for complete search history.

(56) References Cited

U.S. PATENT DOCUMENTS 3,813,434 A    5/1974   Marans
4,554,376 A *  11/1985  Fujimoto et al. ............ 562/554
5,049,283 A    9/1991   Hasselbach et al.

FOREIGN PATENT DOCUMENTS

FR    2 772 026    6/1999
JP    29-8677      12/1954

(Continued)

OTHER PUBLICATIONS

"Practical Ion Exchange", *Orugano Kabushiki Kaisha*, pp. 74-88 (1972).

(Continued)

*Primary Examiner*—Karl J Puttlitz
(74) *Attorney, Agent, or Firm*—Staas & Halsey LLP

(57) ABSTRACT

The present invention provides a method for purifying an amino acid contained in an aqueous solution of alkali metal salt of amino acid comprising the steps of: (1) cation exchanging, which comprises subjecting an aqueous solution of alkali metal salt of amino acid to a desalting purification treatment using a moving bed type continuous ion exchange apparatus comprising a cation exchange resin to obtain an aqueous solution of crude amino acid; and (2) anion exchanging, which comprises adsorbing to a weakly basic anion exchange resin an iminodicarboxylic acid, which is a coexisting by-product, in the resulting aqueous solution of crude amino acid to remove the iminodicarboxylic acid, wherein the aqueous solution of crude amino acid is passed even after adsorbing the iminodicarboxylic acid to the break through point of the weakly basic anion exchange resin.

18 Claims, 7 Drawing Sheets

FOREIGN PATENT DOCUMENTS

| | | |
|---|---|---|
| JP | 36-21315 | 11/1961 |
| JP | 38-5104 | 4/1963 |
| JP | 43-29929 | 12/1968 |
| JP | 51-34114 | 3/1976 |
| JP | 51-24481 | 7/1976 |
| JP | 51-40044 | 11/1976 |
| JP | 52-118421 | 10/1977 |
| JP | 54-1686 | 1/1979 |
| JP | 57-53775 | 11/1982 |
| JP | 58-8383 | 2/1983 |
| JP | 58-8384 | 2/1983 |
| JP | 58-210027 | 12/1983 |
| JP | 59-28543 | 7/1984 |
| JP | 59-118747 | 7/1984 |
| JP | 2-9018 | 2/1990 |
| JP | 2-9019 | 2/1990 |
| JP | 2-215746 | 8/1990 |
| JP | 2255647 | * 10/1990 |
| JP | 7-68191 | 7/1995 |
| JP | 9-3015 | 1/1997 |
| JP | 9-67322 | 3/1997 |
| JP | 2003-212829 | 7/2003 |
| JP | 2003212829 | * 7/2003 |
| JP | 2003-221370 | 8/2003 |

OTHER PUBLICATIONS

"Proceedings of the Japan Academy", *Japan Academy*, vol. 30, No. 2 (Feb. 1954).

G. Albrecht et al., "The Crystal Structure of Glycine", pp. 1087-1103 (May 1939).

English language abstract of Japanese Patent Publication No. 2003-221370, published Aug. 5, 2003.

English language abstract of Japanese Patent Publication No. 49-13115, published Feb. 5, 1974.

Supplementary European Search Report, mailed Mar. 5, 2008 and issued in corresponding European Patent Application No. 05728824.3-1211.

* cited by examiner

RESULTS                                    PLES)

METHOD FOR PURIFICATION OF AMINO ACID

CROSS-REFERENCE TO RELATED APPLICATIONS

This application is based on and hereby claims priority to PCT/JP2005/006753 filed on Apr. 6, 2005 and Japanese priority application Nos. 2004-113554 and 2004-163593 filed on Apr. 7, 2004 and Jun. 1, 2004 respectively, the contents of which are hereby incorporated by reference.

TECHNICAL FIELD

The present invention relates to a method for purifying amino acids widely used as starting materials for food additives, medicines, agricultural chemicals, etc. More particularly, the present invention relates to a method for purification of amino acid comprising the steps of subjecting an alkali metal salt of amino acid to a desalting purification treatment using ion exchange resins; and removing iminodicarboxylic acid from the aqueous solution. Furthermore, the present invention relates to a method for purification of amino acid comprising the step of crystallizing only γ-type glycine or α-type glycine in the case of the amino acid being glycine.

BACKGROUND OF THE INVENTION

[1] Background art on desalting purification of an aqueous solution of an alkali metal salt of amino acid:

The method for producing an amino acid, such as glycine or alanine, which comprises reacting cyanohydrin with ammonia and hydrolyzing aminonitrile corresponding to the resulting amino acid (glycinonitrile in the case of glycine and aminopropionitrile in the case of alanine) is known as a Strecker reaction. The method is disclosed, for example, in JP-B-29-8677, JP-B-59-28543, JP-B-51-24481, JP-B-43-29929 and JP-B-51-40044. In the Strecker method, amino acid is obtained in the form of an alkali metal salt.

As a method for producing amino acid from the resulting aqueous solution of alkali metal salt of amino acid, there has been proposed a method which comprises neutralizing the aqueous solution of alkali metal salt of amino acid with sulfuric acid and thereafter recovering amino acid by crystallization method. According to the crystallization method, because inorganic salts, such as sodium sulfate and sodium chloride, which are produced, for example, in purification of an aqueous solution of sodium salt of glycine, are very similar to glycine in solubility, the amino acid, namely, glycine, cannot be sufficiently recovered by one-stage crystallization. Therefore, the following various methods have been proposed. That is, there are methods which carry out a series of troublesome operations such as crystallization of a part of the inorganic salt by troublesome adjustment of pH, crystallization of a part of iminodiacetic acid, and crystallization of glycine (see, for example, JP-B-58-8383, Japanese Patent No. 1179351 and JP-A-52-118421); and methods which repeat a plurality of times the operation of crystallizing a part of sodium sulfate at high temperatures and then crystallizing glycine at low temperatures (see, for example, JP-B-57-53775). However, all of these methods are very troublesome in operation and low in productivity, and can hardly be industrially employed.

On the other hand, there have been proposed methods of obtaining an aqueous amino acid solution by subjecting alkali metal ions in an aqueous solution of alkali metal salt of amino acid to cation exchanging (desalting) using a cation exchange resin. Methods using weakly acidic cation exchange resins are disclosed in JP-B-29-8677, JP-B-36-21315 and JP-A-2003-221370, and a method of using a strongly acidic cation exchange resin is disclosed in JP-B-7-68191.

In general, the ion exchange resins used are required to have a different adsorbability for alkali metals than adsorbability for amino groups of amino acid, namely, have selectivity in adsorption for them. Therefore, in order to avoid adsorption of amino groups of amino acid to the resin as much as possible, weakly acidic cation exchange resins will be suitable.

Furthermore, as for ion exchange apparatuses using ion exchange resins, there are proposals to reduce the absolute amount of the resin used and improve ion exchange efficiency and regeneration efficiency by continuously moving the resin as compared with a fixed bed type (a moving bed type continuous ion exchange apparatus). For example, a method of moving bed type is proposed according to which a column through which a solution is passed for ion exchange, a column for regeneration, and a column for water washing are organically connected; the resin is automatically discharged by passing the solution under internal pressure of the column, and transferred to the hopper of the next column; then, a resin, in an amount corresponding to the amount of the resin discharged due to reduction of internal pressure of the column caused by extraction of the solution, is introduced into the column from the upper hopper, and the resin, in an amount corresponding to the amount of resin introduced, is automatically and gradually transferred to the hopper from the other column under the internal pressure of the column so as to return to the initial state of solution passing; and this operation is repeated to continuously transfer the resin (see JP-B-38-5104 and Shozo Miyahara, Takaaki Omagari and Shigeo Sakai, "Practical Ion Exchange" pp 74-88 (1972) (Kagaku Kogyosha)).

However, the desalting purification using a moving bed type continuous ion exchange apparatus has been utilized solely for recovery from a dilute ion solution. That is, there have been no proposals to carry out ion exchange from high concentration ion solution, such as desalting purification of an aqueous solution of alkali metal salt of amino acid, by a moving type continuous ion exchange apparatus.

As mentioned above, when desalting purification of an aqueous solution of alkali metal salt of amino acid such as glycine or alanine is carried out using an ion exchange resin, it is advantageous to use a weakly acidic cation exchange resin of H-form, taking into consideration a decrease in product recovery efficiency due to adsorption of amino acid. However, it is known that the weakly acidic cation exchange resin expands (or swells). Generally, strongly acidic cation exchange resins having sulfonic groups as functional groups and comprising a styrene resin as a matrix do not utterly expand (rather contract) in the case of exchanging from H-form to Na-form. On the other hand, it has been reported that, for example, weakly acidic cation exchange resins having carboxylic groups as functional groups and comprising a methacrylic resin as a matrix are 90% in swelling ratio (increase to 1.9 times in volume) in exchanging from H-form to Na-form, and weakly acidic cation exchange resins comprising an acrylic resin as a matrix are 50% in swelling ratio (increase to 1.5 times in volume). When generally employed fixed bed type apparatus is industrially utilized as an ion exchange process, there are the following defects. That is, when the resin abruptly expands in volume, drifting of the solution occurs causing a decrease of ion exchanging reaction efficiency, and furthermore, an extravagant pressure is applied to the resin in the lower part of the column causing serious damage of the resin. Therefore, ion exchange efficiency decreases and frequent addition of the resin is necessary. Moreover, there is a possibility of deformation or breakage of the exchanging column by the pressure generated by expansion of the resin, and special structures are required in the design of exchange apparatuses that consider strength, supply of solution, and recovery of solution.

Thus, use of weakly acidic cation exchange resins causes various problems such as decrease in exchange efficiency and water washing efficiency due to the expansion of the resin, care on inserts and strength in designing of the exchanging column, and the necessity of adding resin owing to damages of the resin. These problems are disadvantageous in industrially carrying out the desalting purification of an aqueous solution of alkali metal salt of amino acid using fixed bed type ion exchange apparatuses. In addition, for purification of amino acid which is to be commercialized finally as a solid, it is necessary to subject to the exchange treatment the solution of raw material (solution to be treated) at a concentration as high as possible and to carry out efficient purification utilizing all of the ion exchange groups. Therefore, when desalting purification of an aqueous solution of alkali metal salt of amino acid is carried out with fixed bed type ion exchange apparatuses, the expansion of the resin occurs throughout the exchanging column and thus, problems caused by the expansion of the resin occur conspicuously.

Moreover, generally, in carrying out ion exchange with fixed type ion exchange apparatuses, passing of the solution is stopped when the concentration of the alkali metal reaches a given value in the aqueous amino acid solution obtained as a product (namely, at a break through point of the ion exchange resin). In this case, the solution to be treated (the raw material) remains in the ion exchanging column as a solution carried by the resin (1 $m^3$ of ion exchange resin contains 0.5 $m^3$ of void water), and for recovery of the solution, pure water is supplied to carry out replacement (forcing out) and water washing. This water used for the water washing contains active ingredients, which are recovered as raw materials, and as a result, the raw materials are diluted. Furthermore, after regeneration of the resin, the resin is similarly washed with water to remove the mineral acids and mineral acid alkali metal salts used as regenerating agents, and then the passing of solution is restarted. In this case, the aqueous solution of the product amino acid is unavoidably diluted than the concentration of the raw material with void water contained in the H-form resin (although the void water can be abandoned before the product amino acid begins to be discharged). The amino acid is usually commercialized as solid, and hence water must be recovered and much dilution is industrially disadvantageous.

Moreover, in carrying out the ion exchange treatment by fixed bed type ion exchange apparatuses, the above-mentioned operation is generally employed, and there occurs unavoidably some leakage of the alkali metal salt into the aqueous solution of the product amino acid. When it is attempted to inhibit the leakage, the exchange treatment is required to terminate before the effective utilization of the tip portion of the packed ion exchange resin. That is, amino groups of the amino acid are partially exchanged and adsorbed to the tip portion of the ion exchange resin column. If the replacement by water washing is carried out excessively, since there is a problem of dilution, the resin to which amino acid partially adsorbs is carried to the regeneration step, which leads to loss of useful amino acid. This further brings about an increase of environmental load due to wastes. For avoiding this problem, JP-A-2003-221370 proposes a method of further feeding the alkali metal salt of amino acid after reaching the break through point and reports that the concentration of amino acid (glycine) in the solution subjected to regeneration treatment is reduced to 110 ppm/$SO_4$. However, this method suffers from the problem of an increase in the amount of the raw material recycled. Moreover, the problem of leakage of alkali metal in the product has not been solved, and the concentration of sodium ion in the product amino acid (glycine) corresponds to 240 wtppm/glycine.

Depending on the production method, the ion exchange resins include those in which one spherical particle is formed by agglomeration of microspheres as a base matrix and those which have a three-dimensional network structure, but have a base matrix which is dense and high in physical strength due to the content of crosslinking agent. The former has a space volume produced by agglomeration of microspheres and hence is high in diffusion rate and ion exchange rate, but low in resin strength and unavoidably has the defects caused by the resin expansion. The latter is somewhat superior in resin strength and hence, is expected to have less problems caused by the resin expansion; but since the base matrix is dense, the resin has a low ion exchange rate and a small selectivity for adsorption of alkali metal and amino group of amino acid, therefore it is difficult to perform efficient recovery of the product amino acid with fixed bed type ion exchange apparatuses.

[2] Background art on separation and recovery of amino acid and iminodicarboxylic acid:

In producing amino acid by Strecker method, there is a demand to separate and recover simultaneously and at high purity the iminodicarboxylic acid, which is a by-product in the reaction, and the amino acid, which is a product. As mentioned above, the attempt to purify amino acid by crystallization method has not succeeded in the conventional technologies.

A method of crystallization and recovery of amino acid as a copper salt has been proposed, but this method requires troublesome operation for removing copper (see, for example, JP-A-59-118747). According to a method of utilizing an electrodialysis with ion-exchange membranes, amino acid of high purity can be obtained. However, amino acid permeates through the membrane and is contained in the discharged solution, and membranes through which only multivalent ions of iminodicarboxylic acid selectively permeate have not been developed, and hence, the above method cannot be industrially utilized (see, for example, JP-A-51-34114).

Furthermore, a method of adsorbing amino acid to H-form strongly acidic cation exchange resins and thereafter separating the amino acid has been proposed (see, for example, JP-A-58-210027). This is conducted in a laboratory, but requires a large amount of ion exchange resins for adsorption of a large amount of amino acid, and can hardly be industrially employed. A method of carrying out chromatographic separation using strongly acidic cation exchange resins of salt form has been proposed (see, for example, JP-A-2-215746), but it is difficult to continuously treat a large amount of a solution in industrial scale, and a great number of ion exchange columns are required. Any of these conventional technologies have no disclosures of a process in which amino acid and iminodiacetic acid can be simultaneously separated and recovered at high purity and high yield.

Furthermore, there has been proposed a method according to which sodium ions of an aqueous solution of sodium salt of amino acid are subjected to cation exchanging (desalting) using a cation exchange resin to obtain an aqueous solution of crude glycine containing a colored substance, followed by treating with a weakly basic anion exchange resin or a medium basic ion exchange resin (see, for example, JP-B-54-1686).

This document has no disclosure on purity (residue of impurity) of the resulting amino acid (glycine), but discloses that the loss of glycine adsorbed to the ion exchange resin is about 0.2-1.5%. The purity of the resulting amino acid is kept by stopping the passing of solution when the concentration of organic acid (iminodiacetic acid, glycolic acid, formic acid) contained reaches a specified value, namely, a break through point at which the organic acid in a given amount leaks in anion exchanging. In this case, since the break through point in adsorption of organic acid is not a saturated adsorption point of the anion exchange resin, the organic acid does not adsorb with saturation to the tip of the anion exchange resin, and there is an ion exchange region which has not been subjected to exchanging. That is, in this ion exchange region, anions of amino acid are ion exchanged and adsorbed to the anion exchange resin in addition to OH-form anions.

When this ion exchange region is regenerated with an alkali metal salt, anions in amino acid are ion exchanged and carried together with the regeneration solution, resulting in recovery loss of amino acid. Moreover, the recovery solution contains iminodiacetic acid in a large amount, and iminodiacetic acid can be produced as a product. However, amino acid incorporates into the product as an impurity, and thus complicated operation is necessary.

Furthermore, in general, iminodiacetic acid adsorbed to the resin in the column is liberated by chromatographic separation and regeneration with a solution of a base which is sodium hydroxide, and hence, iminodiacetic acid is obtained in the form of a sodium salt. Therefore, in the case when a product iminodiacetic acid in the form of an acid is desired, a purification step is further needed, which greatly affects the cost.

[3] Background art on purification of glycine:

Amino acids, especially glycine, are widely used as raw materials for food additives of processed foods, medicines, and agricultural chemicals.

The background art relates to a method for production of glycine, in more detail, a method for optionally producing glycine in a desired crystal form. The crystal forms of glycine include the three forms of α, β, γ types (see, for example, "J. Amer. Chem. Soc." 61, 1087 (1939) and "Proc. Japan Acad." 30, 109 (1954)). There is a demand for a method of optionally purifying glycine to a desired form (α-type glycine or γ-type glycine).

As a method for industrial isolation of glycine, concentration crystallization, cooling crystallization, solvent crystallization, and the like are generally carried out, and the product is commercialized as α-type glycine. The α-type glycine is high in luminance and smaller in average particle diameter than γ-type glycine, and hence, is demanded to be commercialized from the viewpoint of the uses for food additives, etc.

However, it has become clear that this α-type glycine is apt to firmly consolidate in the form of rocks during storage, which causes serious problems in production, distribution and storage, and uses. This is due to the transition of α-type glycine to γ-type glycine in the presence of water.

Under the circumstances, in order to avoid the problem of consolidation of α-type glycine, there has been proposed a method of previously obtaining glycine as γ-type glycine. For example, JP-B-2-9018 discloses a method for producing γ-crystal glycine by inoculating γ-crystal in a saturated solution of glycine and gradually cooling the solution while stirring. This is a proposal that γ-type glycine can be produced by inoculating γ-type glycine in a saturated solution of glycine.

However, according to the example given in the patent document, it is disclosed that the method is fundamentally batchwise, and γ-type glycine is stably obtained when the cooling rate is 5° C./Hr while α-type glycine is produced when the cooling rate is 50° C./Hr. That is, it is presumed that a mixture of α-type glycine and γ-type glycine is obtained depending on the gradual heating rate. γ-type glycine is stably obtained under the conditions of a gentle cooling rate of 5° C./Hr, and when the method is industrially carried out, a large-sized crystallizing cell or many crystallizing cells are required, which is disadvantageous. In order to selectively produce only the desired crystal form of α-type glycine or γ-type glycine, the gradual heating rate must be accurately controlled. Moreover, the patent document is silent on the quality of water used for crystallization. (Hereinafter, "α-type glycine" and "γ-type glycine" are sometimes referred to as merely "α-type" and "γ-type", respectively.)

JP-A-9-67322 reports a method for producing γ-type glycine under quenching comprising keeping the degree of supersaturation in operation in the crystallizing cell at 0.1-2.0 g glycine/100 g water. However, this method also requires severe control of the degree of supersaturation. It is disclosed in the specification that if it deviates from the range of control, a mixed type glycine of α-type and γ-type is obtained, and this is not satisfactory as a method for industrial production of glycine having the desired crystal form. Moreover, this patent document makes no mention of the quality of water used for crystallization.

Moreover, there has been proposed a method of converting crystallized α-type glycine to γ-type glycine.

For example, JP-B-2-9019 proposes that α-type glycine in the state of crystal, which is kept coexistent with γ-type glycine and water, be converted to γ-type glycine. However, as mentioned in this patent document, the method has the defects that agglomeration and consolidation are apt to occur during conversion of α-type glycine to γ-type glycine, and troublesome operations such as grinding are required for obtaining γ-type glycine as commercialized products by industrially carrying out the method. Moreover, the patent document makes no mention of the quality of water used for crystallization.

JP-A-9-3015 proposes that α-type glycine is kept in an aqueous solution having a pH of 7-14 and converted to γ-type glycine in the state of crystal. However, as mentioned above, there are problems that agglomeration and consolidation are apt to occur during conversion of α-type glycine to γ-type glycine, and troublesome operations such as grinding are required for obtaining γ-type glycine as commercialized products by industrially carrying out the method. Furthermore, the patent document proposes to add hydroxides, carbonates, or oxides of alkali metals or alkaline earth metals to aqueous glycine solution. However, the object of the addition is merely to convert α-type glycine to γ-type glycine by adjusting the pH of the aqueous glycine solution to 7-14. In the examples given in the patent document, only sodium hydroxide was used.

SUMMARY OF THE INVENTION

The first object of the present invention, relating to the above-mentioned "[1] Background art on desalting purification of an aqueous solution of an alkali metal salt of amino acid", is that in carrying out desalting purification of an alkali metal salt of amino acid with a weakly acidic cation exchange resin, various problems caused by expansion of the resin are avoided, simultaneous dilution of the product solution is markedly inhibited, and, besides, the amount of amino acid incorporating into aqueous solution of alkali metal salt of a mineral acid used for regeneration is sharply reduced. In addition, the object of the present invention is to attain efficient purification of amino acid even with using an ion exchange resin which cannot attain efficient purification of amino acid by the usual fixed bed type process.

The second object of the present invention, relating to the above-mentioned "[2] Background art on separation and recovery of amino acid and iminodicarboxylic acid", is to provide a method which can industrially and simply separate and purify amino acid and iminodicarboxylic acid in the form of acid at high purity and high yield from an aqueous solution containing amino acid and iminodicarboxylic acid.

The third object of the present invention, relating to the above-mentioned "[3] Background art on purification of glycine", is to provide a simple method for purifying glycine which comprises crystallizing α-type glycine or γ-type glycine in a desired crystal form without producing a mixture of α-type and γ-type in industrial purification of glycine crystals.

The inventors have found that the first object can be attained by using a moving bed type continuous ion exchange apparatus in a cation exchange step where an aqueous solution of crude amino acid is obtained by subjecting an aqueous solution of alkali metal salt of amino acid to a desalting purification treatment using a continuous ion exchange apparatus containing an ion exchange resin (step (1)).

Furthermore, the inventors have found that the second object can be attained in the following manner. That is, in an anion exchange step where iminodicarboxylic acid, which is a coexisting by-product in the resulting aqueous solution of crude amino acid, is adsorbed to a weakly basic anion exchange resin and removed from the aqueous solution of crude amino acid, the aqueous solution of crude amino acid is passed even after the iminodicarboxylic acid is adsorbed up to the break through point of the weakly basic anion exchange resin to carry out ion exchanging of iminodicarboxylic acid to recover the amino acid adsorbed to the weakly basic ion exchange resin (step (2)).

In addition, the inventors have found that the third object can be attained by using water containing no multivalent cations or water containing at least one kind of multivalent cations in an amount of at least 15 μmol/L as a solvent for crystallization in a glycine purification step where only γ-type glycine or only α-type glycine is crystallized from an aqueous solution containing glycine which has been subjected to the above steps (1) and (2) (the step (3) or (4)).

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
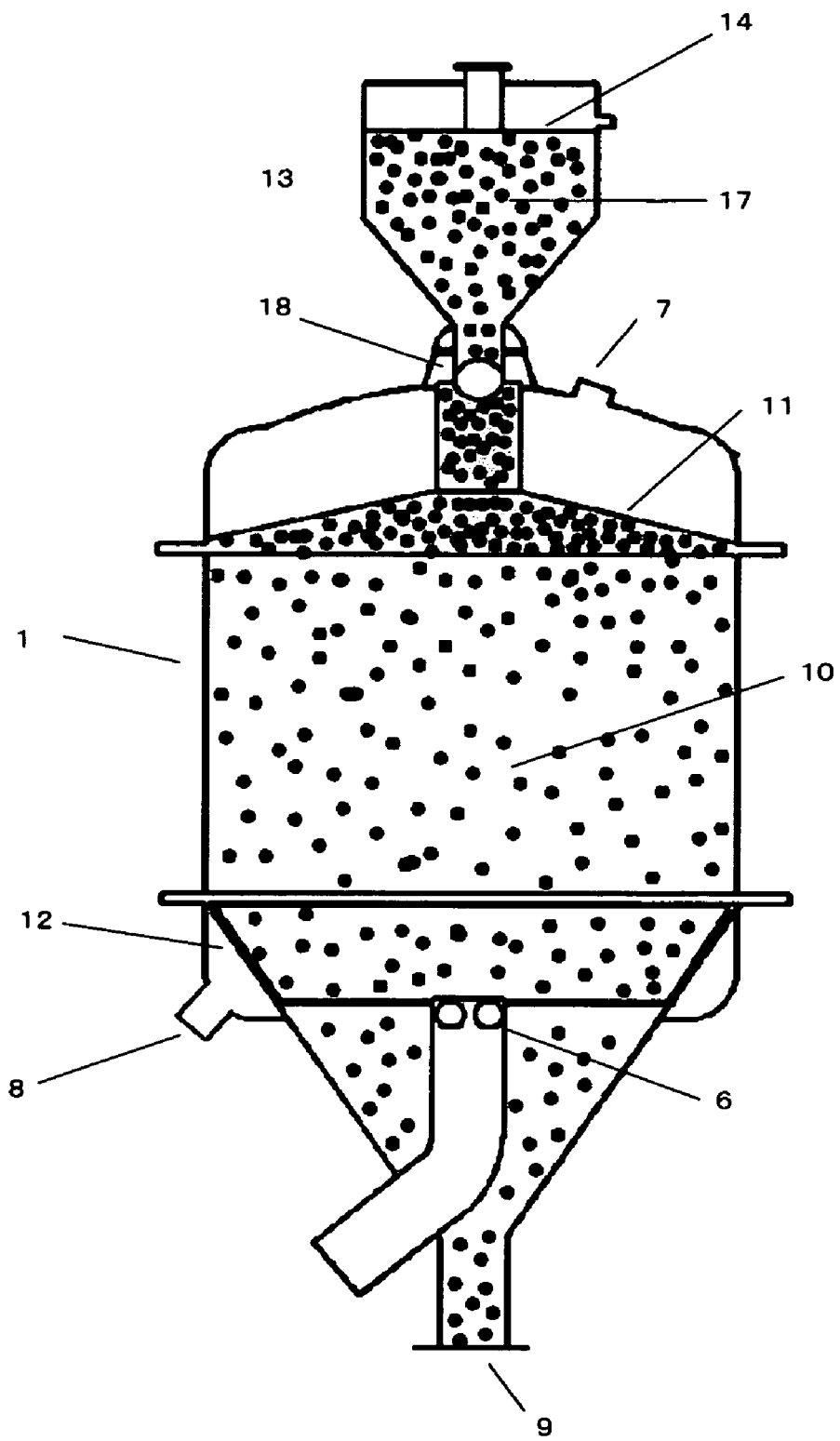
FIG. 1 shows one example of the structure of the exchange column in industrially carrying out step (1) of the present invention.

The present invention has the following constructions.

[1] A method for purification of amino acid from an aqueous solution of alkali metal salt of amino acid comprising the steps of:

(1) cation exchanging, which comprises subjecting an aqueous solution of alkali metal salt of amino acid to a desalting purification treatment using a cation exchange resin to obtain an aqueous solution of crude amino acid, wherein said cation exchanging is carried out using a moving bed type continuous ion exchange apparatus; and (2) anion exchanging, which comprises adsorbing to a weakly basic anion exchange resin an iminodicarboxylic acid, which is a coexisting by-product, to remove the iminodicarboxylic acid from the resulting aqueous solution of crude amino acid, wherein the aqueous solution of crude amino acid is passed even after adsorbing the iminodicarboxylic acid to the break through point of the weakly basic anion exchange resin to carry out anion exchanging with the iminodicarboxylic acid, thereby recovering the amino acid adsorbed to the weakly basic anion exchange resin.

[2] A method described in [1], wherein the step (2) comprises a series of the following steps for recovering amino acid from the aqueous solution of crude amino acid containing iminodicarboxylic acid:

a) contacting the aqueous solution of crude amino acid containing iminodicarboxylic acid with a weakly basic anion exchange resin to subject the by-product iminodicarboxylic acid to ion exchanging, thereby producing an aqueous solution of amino acid;

b) further successively contacting the aqueous solution of crude amino acid containing iminodicarboxylic acid with the weakly basic anion exchange resin even after adsorbing the iminodicarboxylic acid to the break through point of the weakly basic anion exchange resin, thereby ion exchanging the amino acid trapped by the weakly basic anion exchange resin with iminodicarboxylic acid to recover amino acid, c) forcing out and washing with water the aqueous solution containing amino acid which remains in the weakly basic anion exchange resin, d) flowing water from the bottom part of the weakly basic anion exchange resin to carry out back washing, e) regenerating the weakly basic anion exchange resin by contacting an aqueous solution of alkali metal hydroxide with the weakly basic anion exchange resin, and f) forcing out and washing with water the aqueous solution containing alkali metal salt of iminodicarboxylic acid which remains in the weakly basic anion exchange resin.

[3] A method described in [1] or [2], wherein amino acid comprises at least one selected from the group consisting of glycine, alanine, and methionine.

[4] A method described in [1] or [2], wherein the cation exchange resin used in the step (1) is a weakly acidic cation exchange resin.

[5] A method described in [1] or [2], wherein the moving bed type continuous ion exchange apparatus used in the step (1) comprises at least three columns of 1: an exchange column which carries out ion exchange reaction, 2: a replacing column which replaces the solution carried by the ion exchange resin, and 3: a regeneration column which regenerates the resin exchanged with alkali metal ions to an H-form resin with an aqueous solution of mineral acid supplied.

[6] A method described in [1] or [2], wherein the iminodicarboxylic acid comprises at least one acid selected from the group consisting of iminodiacetic acid, iminodipropionic acid, and iminodi-4-methylthiobutyric acid.

[7] A method described in [3], wherein the amino acid comprises glycine.

[8] A method described in [7], wherein the combination of amino acid and iminodicarboxylic acid is a combination of glycine and iminodiacetic acid and the aqueous solution of crude amino acid contains glycolic acid and/or formic acid in addition to iminodiacetic acid as by-products.

[9] A method described in [7] or [8] further comprising the step (3): purifying glycine by crystallizing only γ-type glycine from the aqueous solution containing glycine which has been subjected to the steps (1) and (2), wherein water containing no multivalent cation is used as a solvent for crystallization.

[10] A method described in [7] or [8] further comprising the step (4): purifying glycine by crystallizing only α-type glycine from the aqueous solution containing glycine which has been subjected to the steps (1) and (2), wherein water containing at least one kind of multivalent cation in an amount of at least 15 μmol/L is used as a solvent for crystallization.

DESCRIPTION OF THE PREFERRED EMBODIMENTS

First, a specific embodiment relating to the above step (1) will be explained.

The step (1) is a method of carrying out desalting of an alkali metal salt of amino acid (typically glycine) using "a moving bed type continuous ion exchange process (apparatus)". One example of the desalting can be shown by the following formulas.

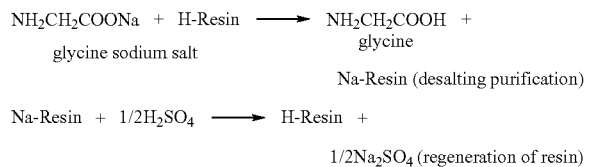

The ion exchange resin which has been used for the above exchange reaction is subjected to liquid replacement (recovery of raw material), regeneration (treatment with sulfuric acid to return to H-form), and again liquid replacement (prevention of dillution of amino acid solution due to void water) while being transferred from the exchange column through the respective columns and returns to the exchange column.

The ion exchange apparatus used in the step (1) is preferably such one as disclosed in JP-B-38-5104, namely, a moving bed type continuous ion exchange apparatus which is characterized in that a column through which a solution is passed for ion exchange, a column for regeneration, and a column for water washing are organically connected; the resin is automatically discharged and transferred to the hopper of the next column by the internal pressure of the column generated by passing the solution; then, a resin, in an amount corresponding to the amount of the resin discharged due to reduction of the internal pressure of the column caused by extraction of the solution, is introduced into the column from the upper hopper; a resin, in an amount corresponding to the amount of the resin introduced, is automatically and gradually transferred to the hopper from other column under the internal pressure of the column to return to the initial solution passing state; and this operation is repeated to continuously transfer the resin.

Figure 2:
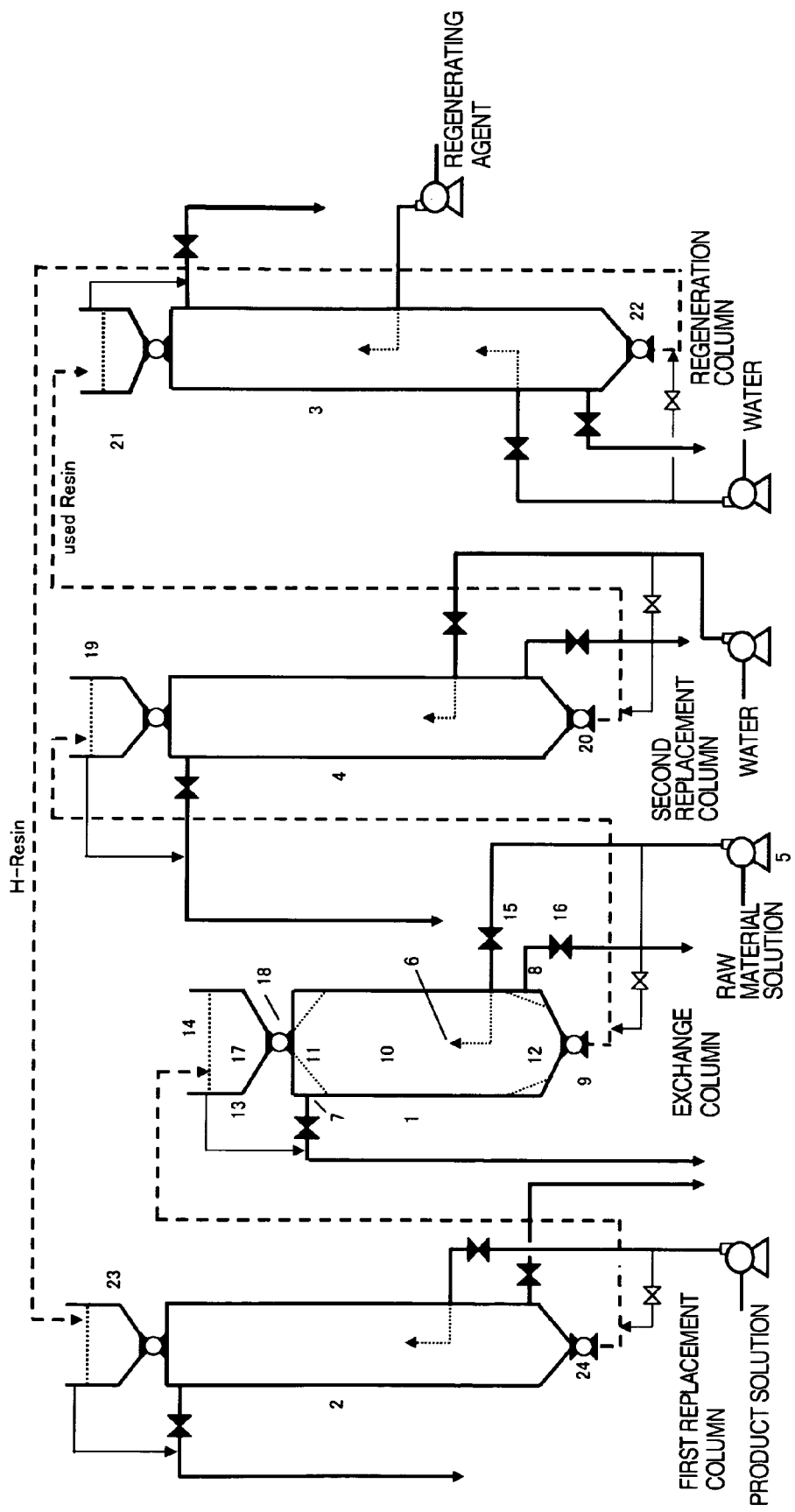
FIG. 2 shows one example of a process flow in industrially carrying out the step (1) of the present invention.

A preferred construction of the column in the ion exchange apparatus in the step (1) comprises at least three columns including an exchange (adsorption) column in which an ion exchange reaction is carried out; a replacement column in which a solution carried by the ion exchange resin is replaced; and a regeneration column in which the resin subjected to exchange with alkali metal ions is regenerated to H-form by supplying an aqueous solution of mineral acid. As a preferred example, as shown in FIG. 2, an ion exchange apparatus is used which comprises an exchange (adsorption) column 1, in which an ion exchange reaction is carried out, a second replacement column 4, in which the solution carried by the ion exchange resin subjected to exchanging is replaced with water and the solution to be treated (raw material) is recovered, a regeneration column 3, in which the resin exchanged with alkali metal ions is regenerated to H-form by supplying an aqueous solution of mineral acid and the solution carried by the regenerated resin is replaced with water, and a first replacement column 2, in which the solution carried by the regenerated H-form ion exchange resin is replaced with an aqueous amino acid solution (an aqueous solution of crude amino acid which is a product solution in step (1) and which is subjected to step (2) after step (1)) to inhibit dilution of the product solution. In FIG. 2, in the regeneration column, the regenerating agent is supplied at the intermediate stage and pure water is supplied at the lower stage, and regeneration of the ion exchange resin and solution replacement of the regenerated resin are carried out in one column, but naturally two columns including a regeneration column and a replacement column may be employed. Similarly, the exchange column and the second replacement column may be combined into one column. Moreover, if dilution of the aqueous amino acid solution can be allowed, the first replacement column may be omitted.

One example of industrially carrying out the step (1) will be explained in detail referring to the drawings. The term "moving bed type" in this specification means a type of ion exchange apparatus in which the resin is present in the form of a bed in the tank and the resin transfers while maintaining its form. The raw material solution introduced into the exchange column 1 from the raw material inlet 6 by the solution feeding pump 5 contacts with the ion exchange resin 10 present in the form of a bed inside the column while the solution rises in the exchange column and an ion exchange reaction takes place, and thereafter the treated solution (aqueous amino acid solution) is discharged from the treated solution outlet 7 through the filter 11.

In this case, the inside of the column is kept at a given pressurized state by the raw material solution introduced by the pump. The resin used for ion exchanging is automatically sent under the internal pressure from the resin outlet 9 provided at the bottom of the column to the hopper 19 provided at the top of the second replacement column together with the solution in the column. After this operation is continued for a suitable period, the solenoid valve 15 for feeding the solution is closed by the working of a cycle timer. Simultaneously therewith, the solenoid valve 16 for extraction of the solution is opened to automatically discharge a part of the solution in the column from the solution extraction port 8 through the filter 12 by the internal pressure and a head. Thus, as the fluid pressure in the column lowers, the sending of the resin under pressure to the second replacement column is stopped and besides, the resin 17, which has been subjected to regeneration and solution replacement (the solution carried by the resin has been replaced with aqueous amino acid solution in the first replacement column) and is stored in the hopper 13 provided at the top of the column, is introduced into the exchange column through the check valve 18 such as ball valve or butterfly valve by the difference in head.

After lapse of a suitable time, the solenoid valve 16 for extraction of solution is closed again by the working of a timer. Simultaneously therewith, the solenoid valve 15 for feeding solution is opened to start the passing of solution, and thus, the pressure in the column increases to close the check valve. As a result, introduction of the resin from hopper stops, and the resin in the lower part of the column is again gradually fed under pressure to the second replacement column. Similarly, the resin which has been subjected to regeneration and replacement and which is in an amount corresponding to the amount of the resin introduced into the exchange column from the hopper is automatically gradually discharged from the lower resin outlet 24 of the first replacement column and fed to the exchange column. A filter 14, which passes only solution, is provided at the upper part of the hopper. The resin fed under pressure into the hopper of the exchange column from the first replacement column is no longer introduced when the resin is filled in the hopper up to the filter of the upper part of the hopper, and hence, the introduction is automatically stopped due to the balancing of internal pressure.

The same relation as mentioned above can be applied to the transfer of the resin from the exchange column to the second replacement column, from the second replacement column to the regeneration column, and from the regeneration column to the first replacement column. The transfer of the resin and the solution in the respective columns is carried out in utterly the same mechanism as in the exchange column. The size of the columns is optionally set depending on the conditions specific to the respective columns, such as regeneration efficiency, replacement efficiency, exchange speed, etc. According to such method of resin transfer, the resin is transferred by mere head or fluid pressure without using mechanical transfer apparatus, and substantially no damage of the resin is caused.

When the moving bed type continuous ion exchange apparatus as mentioned above is used in the step (1), theoretically, only the resin can be transferred downwardly without transferring the solution, and hence replacement efficiency of the solution is extremely high.

Into the first replacement column of the ion exchange apparatus in the step (1) is introduced the H-form resin subjected to regeneration treatment, which contains water as a void solution from the hopper at the top of the column. On the other hand, an aqueous amino acid solution is supplied from the bottom of the column, and the void solution in the resin layer is replaced with the aqueous amino acid solution. Therefore, the aqueous amino acid solution can be inhibited from being diluted due to the introduction of the void solution (water) of the regenerated resin into the exchange column. Substantially, amino acid is adsorbed to the H-form resin in the lower part of the column through amino group of amino acid. Therefore, the total concentration of amino acid, which is contained in the void solution of the resin layer transferred from the bottom of the column to the exchange column, and amino acid adsorbed to the resin (the adsorbed amino acid is exchanged with alkali metal ions in the exchange column and released) is never diluted to less than the concentration of the aqueous amino acid solution supplied to the first replacement column.

Into the second replacement column of the ion exchange apparatus in the step (1) is introduced the alkali metal ion exchange resin subjected to the exchange reaction in the state of containing the raw material aqueous solution of alkali metal salt of amino acid as a void solution from the hopper at the top of the column. The alkali metal ion exchange resin, in the state of containing water as a void solution, is transferred from the bottom of the column to the regeneration column. Theoretically, the void solution of the resin layer can be replaced by transferring only the resin without transferring the solution when pure water in an amount corresponding to the amount of the solution carried by the resin introduced from the hopper is supplied. In order to further reduce the concentration of alkali metal salt of amino acid in the void solution of the alkali metal ion exchange resin at the outlet of the replacement column, some amount of the water for replacement may be supplied in excess. Specifically, the amount of water for replacement is 0.1-0.5 times (preferably 0.15-0.25 times) the circulation amount of the resin. As a result, since the amount of amino acid leaking into the aqueous solution of alkali metal salt of mineral acid caused during regeneration of the resin can be markedly reduced, loss of useful amino acid can be diminished and, besides, environmental load can be reduced.

Into the exchange column (adsorption column) of the ion exchange apparatus in the step (1) is introduced from the hopper the H-form resin containing the aqueous amino acid solution as a void solution and transferred from the first replacement column. An aqueous solution of alkali metal salt of amino acid is supplied from the bottom of the column, and an ion exchange reaction is carried out in the column. The desalted aqueous amino acid solution is recovered from the top of the column, and the ion exchange resin used for the ion exchange reaction in the state of containing, as a void solution, the raw material aqueous solution of alkali metal salt of amino acid is transferred to the second replacement column from the bottom of the column. In order to complete the ion exchange reaction (to complete the desalting purification), the amount of the ion exchange resin to be circulated is set so that the total exchange capacity of the ion exchange resin per unit time is at least equal to the amount of alkali metal cations supplied to the process per unit time.

The concentration of the aqueous solution of alkali metal salt of amino acid supplied to the exchange column is not to be too high in view of crystallization of amino acid, generation of heat in the ion exchange reaction (heat of neutralization reaction), adverse effect on the transfer of the resin, and heat resistance of the ion exchange resin. On the other hand, if the concentration is too low, the load on the process for commercialization of amino acid as product becomes great. Therefore, the concentration is usually 0.5-3 eq/L, preferably 1.0-2.5 eq/L, more preferably 1.5-2 eq/L, in terms of concentration of alkali metal ion.

The desalting purification treatment of alkali metal salt of amino acid in the step (1) includes operations of supplying an aqueous solution of alkali metal salt of amino acid to the exchange column, carrying out the ion exchange reaction in the column, and recovering the aqueous amino acid solution (an aqueous solution of crude amino acid which is a product in the step (1)) from the top of the column. The alkali metal in the product is removed (purified) to a concentration of 200 wtppm or less, preferably 100 wtppm or less, more preferably 50 wtppm or less, as a concentration of alkali metal by weight per the product amino acid for enhancing the separation efficiency between the by-product organic acid and the product amino acid at the next step, namely, increasing the purity of the product amino acid.

As the mineral acid used as a regenerating agent of the ion exchange resin in step (1), there may be used sulfuric acid, hydrochloric acid or nitric acid. Incorporation of chloride ion into the product amino acid is not preferred, and nitric acid causes a problem of generating oxygen due to heating; and hence sulfuric acid is preferred.

Into the regeneration column of the ion exchange apparatus in the step (1) is introduced the alkali metal ion exchange resin which has been used for ion exchange reaction, and from which the raw material aqueous solution of alkali metal salt of amino acid has been recovered in the second replacement column, and in which the void solution has been replaced with pure water in the second replacement column. An aqueous solution of mineral acid as a regenerating agent is supplied from the middle part to carry out regeneration of the ion exchange resin, and pure water is supplied from the bottom of the column, thereby carrying out replacement of the void solution of the regenerated H-form resin with pure water. Therefore, the regenerated H-form resin in the state of containing water as a void solution is transferred from the bottom of the column to the first replacement column, and the aqueous solution of alkali metal salt of mineral acid is recovered from the top of the column. In this case, as mentioned above, the concentration of amino acid in the aqueous solution of alkali metal salt of mineral acid recovered is extremely low.

The ion exchange resin used in the step (1) preferably has selectivity in adsorbability for alkali metal and amino group of amino acid. Further, in order to avoid adsorption to the resin as much as possible, it is preferred to use a weakly acidic cation exchange resin. Here, as for the weakly acidic cation exchange resins, generally, those which have carboxylic groups as functional groups and comprise a methacrylic resin as a matrix are 90% in swelling ratio (increase to 1.9 times in volume) and those which comprise an acrylic resin as a matrix are 50% in swelling ratio (increase to 1.5 times in volume) during exchanging from H-form to Na-form. As mentioned above, when a fixed bed type apparatus is industrially utilized, there are the following defects. That is, when the resin abruptly expands in volume, drifting of the solution occurs causing decrease in ion exchanging reaction efficiency and solution replacement efficiency, and furthermore, a large pressure is applied to the resin in the lower part of the column causing serious damage of the resin. Furthermore, the assumption is that the whole resin packed in the resin column is effectively used. That is, expansion of the resin occurs in the whole area of the resin column. However, in the step (1), because the ion exchange reaction is carried out while continuously transferring the ion exchange resin, only a part (10-20% in many cases) of the resin layer, in which the ion exchange reaction actually takes place in the exchange column, shows expansion behavior. Thus, there occurs no problems such as reduction of exchange efficiency due to expansion of resin and rupture of the resin due to pressure loss.

Examples of the weakly acidic cation exchange resins used in the step (1) are AMBERLITE IRC-76 (trademark) manufactured by Organo Co., Ltd., DIAION WK10, WK20 (trademark) manufactured by Mitsubishi Chemical Co., Ltd., and REBATID CNP80 and REBATID CNP-C (trademark) manufactured by BayerAG, etc. Chelate resins such as REBATID TP207 and TP 208 (trademark) manufactured by Bayer AG may also be used.

The ion exchange resins used in the step (1) are those having a strength which can stand transferring of resin in moving bed type continuous apparatuses. Specifically, preferred are weakly acidic cation exchange resins having a crushing strength of 200 g/particle in Na-form. In general, the crushing strength correlates with particle diameter of resin. Therefore, the crushing strength of resin in this specification is a crushing strength of a resin of Na-form having a particle diameter of 600 μm and a pressing break strength per one particle which is measured by a rheometer at a speed of 2 cm/min. The weakly acidic cation exchange resins have a crushing strength of preferably 300 g/particle or more, more preferably 500 g/particle or more, measured as above.

Depending on the production method, the ion exchange resins generally include those in which one spherical particle is formed by agglomeration of microspheres as a base matrix and those which have three-dimensional network structure, but have a base matrix which is dense and high in physical strength due to the content of crosslinking agent. The former has a space volume produced by agglomeration of microspheres and hence, is high in diffusion rate and ion exchange rate but low in resin strength. Therefore, in carrying out ion exchange reaction by fixed bed type apparatus, occurrence of the problems caused by the resin expansion as mentioned above is unavoidable. On the other hand, the latter is somewhat superior in resin strength and hence is expected to have less problems caused by the resin expansion, but as the base matrix is dense, the resin is low in ion exchange rate, and as it is small in selectivity for adsorption of alkali metal and amino group of amino acid, it is difficult to perform efficient recovery of the product by fixed bed type ion exchange apparatuses. However, according to the method of the present invention, the ion exchange reaction is carried out while transferring the resin, and hence, regenerated resin is successively introduced into the exchange column. Therefore, if a proper length of column can be ensured, there are no problems in the efficiency of ion exchange reaction. Accordingly, resins superior in strength can be effectively utilized, and hence, rupture of the resin can be further inhibited. These facts are very advantageous in industrially carrying out the present invention.

The aqueous solution of alkali metal salt of amino acid used in the step (1) is preferably obtained by a chemical synthesis method such as Strecker method. There may also be used an aqueous solution which is a reaction mixture obtained by enzyme reaction of microorganisms and/or reaction of enzyme purified from microorganisms and immobilized enzyme and which contains an alkali metal salt of amino acid. The amino acid which is to be produced by separation in the present invention is a compound differing in relative affinity between the weakly basic anion exchange resin having amino groups used in the step (2) mentioned hereinafter and amino acid and the by-product iminodicarboxylic acid, in adsorbability and liberation ability in replacement for amino acid and carboxyl groups of the iminodicarboxylic acid. As examples of the amino acid, mention may be made of glycine, alanine, methionine, serine, valine, leucine, isoleucine, threonine, cysteine, cystine, phenylalanine, glutamic acid, and aspartic acid, and among them, glycine, alanine, and methionine are preferred.

As the alkali metal salts of amino acid used in the step (1), alkali metal salts of glycine and alanine are preferred. A sodium salt of glycine is especially preferred. The molar ratio of alkali metal to carboxyl group in the aqueous solution of alkali metal salt of amino acid is usually in the range of 1/1-1.2/1. In synthesis of amino acid such as Strecker method, for example, in synthesis of glycine, it is known that iminodiacetic acid, glycolic acid, formic acid, etc. are produced as by-products. These organic acids can be adsorbed and removed by successive treatment with anion exchange resin (the step (2)).

Next, specific embodiments on the step (2) will be explained.

The step (2) relates to an anion exchanging which comprises adsorbing iminodicarboxylic acid which is a coexisting by-product in the aqueous solution of crude amino acid obtained in the step (1) to a weakly basic anion exchange resin to remove the iminodicarboxylic acid, wherein the step is characterized in that the aqueous solution of crude amino acid is passed even after adsorbing the iminodicarboxylic acid to the break through point of the weakly basic anion exchange resin to carry out ion exchanging with the iminodicarboxylic acid, thereby recovering the amino acid adsorbed to the weakly basic anion exchange resin.

The step (2) usually includes a series of the following steps. That is, the steps include: a) contacting the aqueous solution of crude amino acid containing iminodicarboxylic acid with the weakly basic anion exchange resin, thereby ion exchanging the by-product iminodicarboxylic acid to produce an aqueous amino acid solution; b) further continuously contacting the aqueous solution of crude amino acid containing iminodicarboxylic acid with the weakly basic anion exchange resin even after adsorbing the iminodicarboxylic acid until the break through point of the weakly basic anion exchange resin to carry out ion exchanging of the amino acid trapped by the weakly basic anion exchange resin with iminodicarboxylic acid to recover amino acid; c) forcing out and washing with water the aqueous solution containing amino acid which remains in the weakly basic anion exchange resin; d) flowing water from the bottom through the weakly basic anion exchange resin to carry out back washing, e) contacting an aqueous solution of an organic acid stronger in acidity than iminodicarboxylic acid with the weakly basic anion exchange resin to carry out ion exchanging with iminodicarboxylic acid trapped by the weakly basic anion exchange resin, and separating the iminodicarboxylic acid by a chromatograph, thereby producing an aqueous solution of iminodicarboxylic acid; f) regenerating the weakly basic anion exchange resin by contacting an aqueous solution of alkali metal hydroxide with the weakly basic anion exchange resin, and g) forcing out and washing with water the aqueous solution containing alkali metal salt of iminodicarboxylic acid which remains in the weakly basic anion exchange resin.

The iminodicarboxylic acid which is to be separated in the step (2) includes iminodiacetic acid, iminodipropionic acid, iminodi-4-methylthiobutyric acid, or the like.

The step (2) includes a series of the following steps as a specific embodiment. That is, the steps include: a) contacting the aqueous solution of crude glycine containing iminodiacetic acid, glycolic acid, and formic acid as by-products with the weakly basic anion exchange resin to carry out ion exchanging of the by-products iminodiacetic acid, glycolic acid, and formic acid to produce an aqueous glycine solution; b) further continuously contacting the aqueous solution of crude glycine containing iminodiacetic acid, glycolic acid, and formic acid with the weakly basic anion exchange resin even after adsorbing iminodiacetic acid, glycolic acid, and formic acid to the break through point of the weakly basic anion exchange resin to carry out ion exchanging of glycine trapped by the weakly basic anion exchange resin with iminodiacetic acid, glycolic acid, and formic acid to recover glycine; c) forcing out and washing with water the aqueous solution containing glycine which remains in the weakly basic anion exchange resin; d) flowing water from the bottom through the weakly basic anion exchange resin to carry out back washing, e) contacting an aqueous solution of an organic acid stronger in acidity than iminodiacetic acid (e.g., an aqueous solution of formic acid or glycolic acid) with the weakly basic anion exchange resin to carry out ion exchanging with iminodiacetic acid trapped by the weakly basic anion exchange resin and separating the iminodiacetic acid by a chromatograph, thereby producing an aqueous solution of iminodiacetic acid; f) regenerating the weakly basic anion exchange resin by contacting an aqueous solution of alkali metal hydroxide with the weakly basic anion exchange resin, and g) forcing out and washing with water the aqueous solution containing alkali metal salts of iminodiacetic acid, glycolic acid and formic acid which remains in the weakly basic anion exchange resin.

For convenience, the step (2) will be discussed below in only the case where iminodiacetic acid (as a typical example of iminodicarboxylic acid), glycolic acid, and formic acid are contained as by-products. Of course, the content of the step (2) should be defined widely by the content of claim 1 appended hereto, and is not limited to the case where only these compounds are contained.

Generally, the weakly basic anion exchange resins used in the step (2) are preferably those which have a functional group comprising primary, secondary, or tertiary amino group in the molecule and are smaller in ion exchange selectivity coefficient for glycine than for glycolic acid, formic acid, and iminodiacetic acid in order to selectively separate glycine with respect to carboxyl ions of glycolic acid, formic acid, and iminodiacetic acid. Examples of the weakly basic anion exchange resins are AMBERLITE IRA-96SB, IRA-67, XE583, XT6050RF (trademarks) manufactured by Organo Co., Ltd., DIAION WA21, WA30 (trademarks) manufactured by Mitsubishi Chemical Co., Ltd., REBATID MP-62, MP-64, VPOC-1065 (trademarks) manufactured by Bayer AG, PUROLITE A-100, A-103S, A-830, A-845 (trademarks) manufactured by Purolite Co., Ltd., and DOWEX 66, MWA-1, WGR, WGR-2 (trademarks) manufactured by Dow Chemical Corp., etc. The ion exchange group is OH-form. Preferred are weakly basic anion exchange resins having a functional group comprising a secondary amino group and having styrenic resin matrix. Among them, AMBERLITE IRA-96SB is, surprisingly, the highest in recovery efficiency of glycine.

The treatment with weakly basic anion exchange resin is carried out under the condition that the weight of the glycine group in the aqueous solution of crude glycine containing iminodiacetic acid, glycolic acid, and formic acid as by-products is 33% by weight or less. The weight percent of the glycine group may be saturated concentration or less at the operation temperature. In order to obtain the concentration exceeding 33% by weight, the anion exchange resin must be kept at 70° C. or higher, which is not preferred from the point of heat resistance of the weakly basic anion exchange resin. In case these resins are used for the first time, it is necessary to sufficiently carry out pre-treatment and washing with water of the resins for inhibiting incorporation into the glycine, of impurities originating from the resins. The amount of the resins used varies depending on the kinds and amounts of the impurities to be removed. In ion exchanging of organic acid ions of by-products with the weakly basic anion exchange resins, the amount of the resins is usually 1000-5000 ml, preferably 1000-3000 ml, based on 1 kg of glycine to be treated.

The eluent used for chromatographic separation of iminodiacetic acid adsorbed to the ion exchange resin is preferably an organic acid higher in acidity than iminodiacetic acid, and examples of the eluent are formic acid and glycolic acid contained in crude amino acid. Other organic acids may be used so long as they cause no problems in carrying out this process. Specifically, the concentration of aqueous solution of formic acid or glycolic acid used in a series of the processes for separation and recovery of glycine and iminodiacetic acid from aqueous solution of crude glycine, respectively, is 0.5-3 N, preferably 1-2 N. If the concentration is lower, a large amount of water is required for the eluent and the separation pattern of iminodiacetic acid becomes broader. If the concentration is higher, the separation pattern of iminodiacetic acid becomes sharp, but formic acid or glycolic acid as the eluent is incorporated in a large amount.

The regenerating agent used for regeneration of the weakly basic anion exchange resin in the step (2) is an aqueous solution of alkali metal hydroxide. Preferred are aqueous solutions of hydroxides of sodium and potassium as alkali metals. More preferred is an aqueous solution of hydroxide of sodium. The concentration of the aqueous solution of alkali metal hydroxide is 0.5-3 N, preferably 1-2 N. If the concentration is lower, a large amount of water is required for the regenerating agent; and if the concentration is higher, the ion exchange resin is apt to be damaged during regeneration.

The characteristic of the step (2) is that in the step (b), glycine trapped by the weakly basic anion exchange resin and iminodiacetic acid, glycolic acid, and formic acid, which are by-products, are subjected to ion exchanging to recover glycine. A remarkable effect of the step is that substantially no glycine incorporates into the aqueous iminodiacetic acid solution produced by chromatographic separation of iminodiacetic acid trapped by the weakly basic anion exchange resin in the step (e) with an aqueous solution of formic acid or glycolic acid. Therefore, in the series of processes, recovery loss of glycine is very small, and glycine and iminodiacetic acid in the form of an acid can be produced at high purity and high yield, respectively. Furthermore, iminodiacetic acid, formic acid and glycolic acid which are by-products can be saturation adsorbed to the exchange groups of the ion exchange resin, and thus efficiency for removal of by-products is excellent. These characteristics and effects are very advantageous when step (2) is industrially carried out.

A series of processes for separating and recovering glycine from an aqueous solution of crude glycine containing iminodiacetic acid, glycolic acid and formic acid as by-products in step (2) may be a batch type process using one or more ion exchange columns independently.

The treating temperature of the resin is generally room temperature or higher, preferably 20-90° C.

The treating time varies depending on the concentration of the solution to be treated and the size of the ion exchange columns, and is usually 1-6 hr, preferably 1-4 hr in the case of a batch type. When treatment is carried out in continuous manner, the passing rate to the resin column is 1-20, preferably 5-15, in terms of liquid hourly space velocity (UL-resin/Hr).

Next, specific embodiments of steps (3) and (4) will be explained.

The object to be treated in steps (3) and (4) is the aqueous solution containing glycine which has been obtained after subjected to the treatments of steps (1) and (2). It is not intended to limit the amino acid used in steps (1) and (2) to particularly glycine (though typically glycine). On the other hand, the amino acid used in these steps (3) and (4) is limited to glycine.

Furthermore, as glycine used in step (3), there are used those which are obtained by generally known method of amination of monochloroacetic acid, Strecker reaction, hydantoin method, etc., but when the desired product is γ-type glycine, it is necessary that glycine does not contain multivalent cations.

In the steps (3) and (4), crystallization of glycine from a saturated aqueous solution of glycine can be performed by either of continuous crystallization method and batch type crystallization method. Furthermore, in steps (3) and (4), α-type glycine and γ-type glycine can be optionally produced depending on the quality of water used as a solvent for crystallization in the crystallization step. It is known that, β-type glycine cannot be obtained by usual water crystallization.

For obtaining γ-type glycine, water containing substantially no multivalent cations is used as a solvent for crystallization (the step (3)). To contain substantially no multivalent cations means that the multivalent cation concentration in water is preferably 0.2 μmol/L or less. Such water can be easily obtained by an ion exchange treatment and a distillation treatment generally employed in this technical field.

For obtaining α-type glycine, at least one kind of multivalent cations in an amount of at least 15 μmol/L must be dissolved in water used as a solvent for crystallization (the step (4)). In this case, several kinds of multivalent cations may be used in admixture. The amount (a minimum necessary amount for development of the effect) of the multivalent cations is determined depending on crystallization conditions. Addition of multivalent cations in too much amount may cause incorporation into products, and hence the amount is preferably 15-2000 μmol/L, more preferably 50-1000 μmol/L.

The multivalent cations used are not particularly limited, and considering the use of glycine, they are preferably $Ca^{2+}$, $Mg^{2+}$, $Fe^{3+}$, $Zn^{2+}$, $Al^{3+}$, etc., more preferably $Ca^{2+}$ and $Mg^{2+}$. These cations are components to give hardness to water, and are contained in general tap water, for example, as calcium hydrogencarbonate. Therefore, α-type glycine can be produced by using general tap water.

When α-type glycine is obtained by step (4), the multivalent cation added to water used is usually dissolved as a salt of multivalent cation. The kind of the salt is not limited so long as it has the necessary solubility. Examples of the salt are chlorides, hydroxides, nitrates, carbonates, hydrogencarbonates, etc.

It is considered that γ-type glycine can be produced by using ion-exchanged water in steps (3) and (4) because α-type is obtained upon nucleation in the crystallization cell and this is very rapidly converted to thermally stable γ-type glycine in the presence of water. However, when water containing an extremely small amount of multivalent cations is used, surprisingly, the crystals obtained are all α-type glycine. The effects and causes are not clear, but it is considered that an extremely small amount of the multivalent cations exerts a certain influence on mechanism of crystal growth and crystal transition, and nucleation occurs dominantly.

The present invention will be explained on each step by the following examples. These examples should not be construed as limiting the invention in any manner, and various modifications and changes may be made within the scope of the invention as expressed in the appended claims.

First, Examples 1-2 and Comparative Examples 1-2 on the step (1) will be explained.

EXAMPLE 1

Experiment Simulating the Exchange Column

Figure 3:
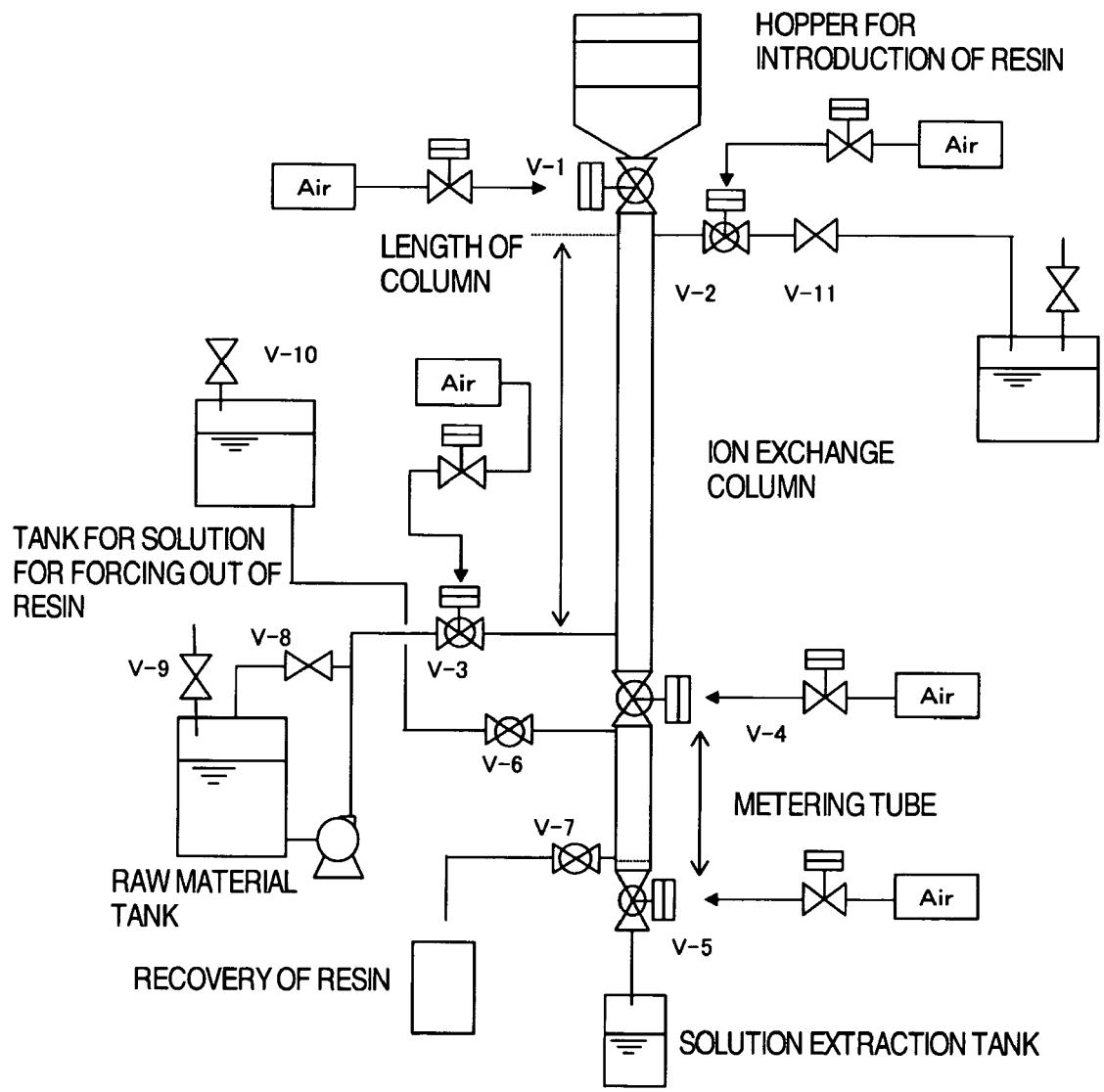
FIG. 3 shows an experimental apparatus simulating the moving bed type continuous ion exchange apparatus used in Example 1 and Example 2.

An ion exchange experiment (including simulating the exchange column) was carried out using an acrylic resin column of 26 mm in inner diameter which simulated a moving bed type continuous ion exchange apparatus. FIG. 3 shows the experimental apparatus used. Valves, V1-5 are air-actuation type ball valves made of a resin and can be opened and closed by a timer cycle control. Filters (folding-woven wire meshes made of stainless steel) were installed to the portions provided with V-2, 3, 5 so as to pass only liquid. The height of the exchange column (height from liquid feeding port to liquid recovering port) was 2 m, and the height of the metering tube (corresponding to the transfer length of resin per 1 cycle) was 34 cm. An H-form weakly acidic cation exchange resin (REBATID CNP-80WS manufactured by Bayer AG; total exchange capacity=4.30 eq/L-Resin (catalog value)) previously immersed in a glycine solution was charged in a hopper for introduction of resin. Thereafter, V-1, 4 were opened to pack the ion exchange resin in the column and the metering tube. An aqueous solution of sodium salt of glycine having the composition as shown in Table 1 was charged in a raw material tank and a tank for a solution used for forcing out of the resin. The operations for ion exchange experiment were as follows. Passing of the solution and extraction of the solution were automatically switched by setting the cycle timer. At the time of passing of the solution, V-3 and V-2 were opened, and solution passing pump P-1 was worked to feed the solution of sodium salt of glycine into the column, and while carrying out the ion exchange reaction, the solution was recovered as a product aqueous glycine solution from the outlet V-11. At the time of extraction of the solution, the pump was stopped and V-3, 2 were closed, and simultaneously V-1, 4, 5 were opened. Therefore, while extracting the solution in the metering tube and the column from V-5, the resin in the column was extracted by head into the metering tube and simultaneously the resin, in an amount corresponding to the amount of extracted resin, was added from the hopper into the column.

In actual industrial operation, the resin falling at the time of extraction of the solution, during passing the solution, was transferred to the next step by the column internal pressure. However, in this experiment, the resin recovered in the metering tube after being used for ion exchanging was recovered from V-7 while introducing the solution to be treated from V-6 during passing of the solution by manual operation. In this example, the amount obtained by subtracting the amount of glycine solution introduced into the column together with the resin from the hopper (50% of apparent volume of the resin+ the amount of the solution recovered from the column at the time of extraction of the solution) from the amount of the raw material solution passed per 1 cycle is the amount of the treated solution of glycine sodium salt per 1 cycle, and the operation was carried out so that the ratio of the amount of the treated solution of glycine sodium salt to the exchange capacity of the introduced resin per 1 cycle (rate of effective use of resin) was 95%.

The above operations were carried out continuously 100 cycles to obtain about 40 L of the product aqueous glycine solution. Analysis of the recovered product solution at every cycle was carried out by a liquid chromatograph. Furthermore, the introduced resin and the recovered resin were subjected to regeneration treatment with aqueous sulfuric acid solution, and the resin adsorption amount was determined by analyzing the regeneration solution. Tables 1-1- 1-4 show the experimental conditions and the results of the above moving bed type continuous ion exchange simulative experiment. The amount of the resin introduced per 1 cycle in this example was 131 ml in terms of H-form resin/water.

During the experiment of this example, there occurred no problems in the behavior of transfer of resin and, besides, removal of Na was very efficiently attained even though an exchange column of high L/D (L/D=77) of 26 mm * 2000 mm was used and the ion exchange resin expanded to about 1.4 times. Furthermore, there occurred neither rupture of resin nor deformation of column due to the pressure loss caused by expansion of resin. The maximum ultimate temperature in the resin layer was 65° C., namely, the temperature was controlled to a temperature that caused no problems in heat resistance of the resin.

From the results of this experiment, it is recognized that according to the method of the present invention, as expansion of the ion exchange resin occurs in only a part of the exchange column, the exchange reaction can be completed without exerting an influence on ion exchange efficiency, for example, occurrence of drift, and as a result, leakage of alkali metal into the aqueous amino acid solution (aqueous solution of crude amino acid which is a product in step (1)) is inhibited and an aqueous amino acid solution of markedly high quality can be obtained. The amount of sodium with respect to glycine in the product solution was 14 wtppm/glycine.

EXAMPLE 2

Experiment Simulating the Second Replacement Column

A replacement experiment (including simulating the second replacement column) was carried out using the experimental apparatus (acrylic resin column) used in Example 1 including simulating the moving bed type continuous ion exchange apparatus. The height of the replacement column (height from solution feeding port to solution recovering port) was 3 m, and the height of the metering tube (corresponding to the transfer length of resin per 1 cycle) was 40 cm. An Na-form weakly acidic cation exchange resin (REBATID CNP-80WS manufactured by Bayer AG) used in Example 1 and previously immersed in a solution of sodium salt of glycine, was charged in the hopper for introduction of resin. Thereafter, V-1, 4 were opened to pack the ion exchange resin in the column and the metering tube. Ion-exchanged water was charged in a raw material tank and a tank for a solution used for forcing out of the resin. The replacing experimental operation was conducted by carrying out continuously 100 cycles in the same manner as in Example 1. No glycine adsorbed to the recovered resin simply by feeding a replacement water in an excessive amount of 0.26 times the amount of circulated resin (the raw material was diluted in corresponding to this amount), and the concentration of glycine in the void solution of the recovered resin and the solution carried by the resin was 18 wtppm, namely, the solution replacement was performed to this concentration. Tables 2-1 to 2-4 show experimental conditions and results of the second replacement column test in this moving bed type continuous ion exchanging. The dilution rate of the raw material aqueous solution of sodium salt of glycine which was determined from the balance of the solution in the example was 0.76.

From the results of this example, it is recognized that according to the method of the present invention, because the solution replacement can be efficiently attained simply by feeding a very small amount of water in excess, the raw material sodium salt of glycine, which is a void solution of the Na-form resin after exchange reaction, can be recovered without excess dilution; on the other hand, substantially no glycine is adsorbed to the Na-form resin sent to the regeneration step, and loss of glycine can be inhibited, and simultaneously the glycine concentration in the aqueous solution of alkali metal salt of mineral acid produced in the regeneration step can be markedly reduced, and thus environmental load of process can be conspicuously diminished. For example, when it is supposed that sulfuric acid in an amount of 1.05 times the equivalent weight of the exchanged Na is used as a regenerating agent, the glycine concentration in the regeneration solution (aqueous sodium sulfate solution) is 110 ppm glycine/$SO_4$.

COMPARATIVE EXAMPLE 1

Fixed Bed Type Ion Exchange Experiment—1:

A fixed bed type ion exchange experiment was conducted using a transparent vinyl chloride resin column of 65 mm in inner diameter and 1500 mm in height (height of resin layer: 825 mm). A solution feeding port was provided at the top part of the column and a solution to be treated was passed through a diaphragm pump. A filter was provided at the flange of the bottom part of the column so as to pass only liquid. The effluent discharged from the solution outlet was recovered while controlling the flow rate by the diaphragm pump. In the column was packed 2750 ml of a weakly acidic cation exchange resin AMBERLITE IRC76 (manufactured by Organo Co., Ltd.) of H-form. The height of the resin layer was 82 cm. An aqueous solution of sodium salt of glycine (containing Na: 6.3% by weight, glycine: 16% by weight, iminodiacetic acid: 1.0% by weight) (Na concentration: 3.1 eq/L) was obtained in the same manner as in Example 1. This aqueous solution was passed in the manner of down flow to obtain an aqueous glycine solution. The raw material feeding temperature was 40° C., and the liquid hourly space velocity (LHSV) of solution passing based on volume was adjusted to 3.0 (L/L/Hr) by controlling the flow rate with an extracting pump. The amount of the aqueous solution of sodium salt of glycine treated per one experiment was 4155 g. That is, the amount of sodium treated in this experiment corresponded to 1.06 times the total exchange capacity of the packed ion exchange resin. Immediately after termination of passing of the aqueous solution of sodium salt of glycine, this was changed over to passing of pure water, which was further continued. The product solution was recovered as fractions of each 250 g at the outlet of the column. Each of the fractions was analyzed, and the fraction in which glycine was firstly observed and additionally the subsequent fractions were recovered as product glycine solutions, and the operation was continued until the Na concentration in the product solutions reached 50 ppm. The same operation was carried out twice. The results are shown in Table 3 (Run. 1 and 2).

In this comparative example, the resin layer expanded to only 880 mm in height during passing of the solution. After changing over to pure water, the resin layer further expanded, and finally the height reached 1000 mm. It was found that the expansion ratio of the ion exchange resin during exchanging to Na-form was 1.6 time, but it expanded to only 1.2 time in the column. Furthermore, when the state of recovery of the bottom solution in the column was observed during the experiment, it was confirmed that flow of the solution in the resin layer of the lower part of the column (wetting of the resin layer) was not uniform at the final stage of passing the solution to be treated. Simultaneously, it was observed that bubbles incorporated into the suction line of the recovery pump for outlet solution. Furthermore, it was confirmed that the column made of vinyl chloride resin deformed at the flange welding portion in the lowermost part of the column.

From the results of this comparative example, it was found that because there was no reproducibility in exchange efficiency in the experiments conducted twice, the vinyl chloride column expanded and deformed, and the flow of the solution in the lower resin layer was not uniform, the resin could not freely expand in the fixed bed type ion exchanging, and an excessive pressure was applied to the resin layer, resulting in drift to cause decrease of ion exchange efficiency.

COMPARATIVE EXAMPLE 2

Fixed Bed Type Ion Exchange Experiment—2:

An experiment was carried out in the same manner as in Comparative Example 1, except that REBATID CNP-80WS (manufactured by Bayer AG) was used as the resin and the amount of the resin packed was 2495 ml. The results are shown in Table 3 (Run.3). In the case of using CNP-80WS, recovery rate of the product glycine per one-pass operation in the fixed bed type ion exchanging was low, namely, about 30% by weight.

On the other hand, separately a cycle of Na-exchanging and regeneration with sulfuric acid was repeated using the weakly acidic cation exchange resin (resin particle diameter: 600 μm) used in the examples and comparative examples, and thereafter, the crushing strength of the Na-form resin was measured by a compression destructive test at a speed of 2 cm/min using a rheometer (NRM2005-J) manufactured by Fudo Kogyo Co., Ltd. The results are shown in Table 4. In the case of using IRC-76, the resin crushing strength of the test product subjected to exchange-regeneration recycling of 100 times decreased to about ½ the strength of a fresh product. On the other hand, in the case of using CNP-80WS, the product showed no change in resin crushing strength even after the recycle test of 1200 times.

From this comparative example, it is considered that REBATID CNP-80WS is superior in resistance against deterioration of resin strength caused by repetition of exchanging-regeneration, but is lower in adsorption selectivity for Na cation and amino group of glycine than IRC-76 and, hence, efficient recovery of products is difficult in fixed bed type ion exchanging. On the other hand, IRC-76 is superior in ion exchangeability, but has problems in resin strength, and there are problems of resin rupture caused by expansion of resin and reduction in efficiency in the fixed bed type ion exchanging as in the comparative example.

Table 1

Conditions and Results of Moving Bed Type Continuous Ion Exchange Simulative Experiment

TABLE 1-1

| <Composition of solution to be treated> | |
|---|---|
| Glycine | 1.77 eq-Acid/L |
| Iminodiacetic acid | 0.14 eq-Acid/L |
| Sodium | 2.04 eq-Na/L |

TABLE 1-2

<Results of analysis on amount of adsorption to ion exchange resin in moving bed type continuous ion exchange experiment>

| | Amount of resin ml/cycle | Glycine | | Sodium | | Resin expansion ratio V/V |
|---|---|---|---|---|---|---|
| | | Adsorption amount eq/L-Resin | Exchange rate % | Adsorption amount eq/L-Resin | Exchange rate % | |
| Introduced resin | 144 | 0.66 | 16.81 | 0.00 | 0.0 | 1.10 |
| Recovered resin | 180 | 0.07 | 2.17 | 2.95 | 94.4 | 1.37 |

TABLE 1-3

<Balance of solutions and experimental conditions in moving bed type continuous ion exchange experiment>

| Time cycle (sec) | | Amount of solution passed (ml/cycle) | Amount of solution carried by resin (ml/cycle) | Amount of treatment solution (ml/cycle) |
|---|---|---|---|---|
| Passing of solution | Extraction of solution | | | |
| 167.0 | 49.0 | 399 | 139 | 260 |

| Amount of treated Na (eq/cy) | Exchange capacity (eq/cy) | Rate of effective use of resin (%) | Na exchange rate of recovered resin (%) |
|---|---|---|---|
| 0.53 | 0.56 | 94.3 | 94.4 |

TABLE 1-4

<Results of moving bed type continuous ion exchange experiment>

| | |
|---|---|
| Amount of product solution | 399 ml/cycle |
| (net amount of treated solution) | (260) ml/cycle |
| Glycine | 2.02 eq-Acid/L |
| Iminodiacetic acid | 0.14 eq-Acid/L |
| Sodium | 2 ppm |
| Na/Glycine | 14 ppm vs glycine |

Table 2
Experimental Conditions and Results in Replacement Column in Moving Bed Type Continuous Ion Exchange

TABLE 2-1

<Solution carried by introduced resin, composition of recovered solution>

| Substrate | | Resin void | Recovered solution | Dilution rate |
|---|---|---|---|---|
| Glycine | eq-Acid/L | 1.80 | 1.47 | 0.82 |
| Imimodiacetic acid | eq-Acid/L | 0.15 | 0.12 | 0.76 |
| Sodium | eq-Na/L | 1.35 | 1.05 | 0.78 |

TABLE 2-2

<Results of analysis on adsorption amount to ion exchange resin in replacement column simulative experiment in moving bed type continuous ion exchange>

| | Amount of resin ml/cycle | Glycine Adsorption amount eq/L-Resin | Glycine Exchange rate % | Sodium Adsorption amount eq/L-Resin | Sodium Exchange rate % | Resin expansion ratio V/V |
|---|---|---|---|---|---|---|
| Introduced resin | 216 | 0.11 | 3.92 | 2.80 | 101.7 | 1.56 |
| Recovered resin | 229 | 0.00 | 0.00 | 2.57 | 97.8 | 1.64 |

TABLE 2-3

<Balance of solution and experimental conditions in replacement column simulative experiment in moving bed type continuous ion exchange>

| Time cycle (sec) | | Amount of solution passed (ml/cycle) | Amount of solution carried by resin (ml/cycle) | Amount of replaced solution (ml/cycle) | Amount of replacement water/amount of circulated resin (V/V) |
|---|---|---|---|---|---|
| Passing of solution | Extraction of solution | | | | |
| 147.7 | 31.8 | 248 | 187 | 61 | 0.26 |

TABLE 2-4

<Results of moving bed type continuous replacement experiment>

| | |
|---|---|
| Void solution in recovered resin | 114 ml/cycle |
| Solution carried by recovered resin | 80 ml/cycle |
| Glycine | 18 ppm |
| Iminodicetic acid | 0 ppm |
| Sodium | 32 ppm |

TABLE 3

Results of experiment of fixed bed type ion exchange

|  | Run. 1 | Run. 2 | Run. 3 |
|---|---|---|---|
| Ion exchange resin | IRC-76 | IRC-76 | CNP-80WS |
| Packing amount of resin ml | 2750 | 2750 | 2495 |
| Total exchange capacity eq | 10.7 | 10.7 | 10.7 |
| Supplied solution to be treated Concentration (wt %) | | | |
| Glycine | 16.0 | 16.0 | 16.0 |
| Sodium | 6.3 | 6.3 | 6.3 |
| Amount of treated solution g | 4155.0 | 4155.0 | 4155.0 |
| Amount of treated Na eq | 11.4 | 11.4 | 11.4 |
| Amount of treated glycine g | 664.8 | 664.8 | 664.8 |
| Treated Na/Resin exchange capacity eq/eq | 1.06 | 1.06 | 1.06 |
| Recovered product glycine solution Concentration (wt %) (wt ppm) | | | |
| Glycine | 11.5 | 12.4 | 11.4 |
| Sodium | 58.0 | 26.0 | 31.3 |
| Amount of product solution g | 3415.0 | 3687.0 | 1720.6 |
| Amount of recovered glycine g | 393.4 | 456.5 | 195.4 |
| One-pass glycine recovery rate g/g | 59.2 | 68.7 | 29.4 |
| Na/glycine (wt ppm) | 503.5 | 210.0 | 275.6 |

TABLE 4

Results of measurement of crushing strength
of weakly acidic cation exchange resin
Na-form resin Resin particle diameter 600 μm

| Ion exchange resin | Exchange-regeneration recycle test number (cycle) | Crushing strength Squeezing strength (g/particle) |
|---|---|---|
| IRC-76 | 0 | 427 |
|  | 104 | 250 |
|  | 193 | 243 |
| CNP-80WS | 0 | 616 |
|  | 111 | 577 |
|  | 200 | 673 |
|  | 400 | 668 |
|  | 1200 | 539 |

Next, Example 3 and Comparative Example 3 on the step (2) will be explained.

Analysis of the recovered solution was conducted by high-speed amino acid analyzing method of o-phthalaldehyde post column process on glycine and iminodiacetic acid. Shim-pack Amino-Na Column (6 mm×100 mm) manufactured by Shimadzu Co., Ltd. and Shimadzu LC-10A-high-speed amino acid analyzing system were used, and detection was carried out by a fluorescent detector manufactured by Shimadzu Co., Ltd. (hereinafter referred to as "OPA analysis"). Analysis on glycolic acid and formic acid was conducted by a pH-buffered post column electric conductivity detection method of Shimadzu Co., Ltd. Shimadzu LC-10A organic acid analyzing system, including Shim-pack Amino-Na Column (6 mm×100 mm), manufactured by Shimadzu Co., Ltd. and a pump LC-10AD manufactured by Shimadzu Co., Ltd. were used, and detection was carried out by electric conductivity detector CDD-10A manufactured by Shimadzu Co., Ltd. (hereinafter referred to as "organic acid analysis").

EXAMPLE 3

Passing of Solution by Batch Type Process

Simulating the aqueous solution of crude amino acid which is obtained in step (1) of the present invention, a simulated solution containing iminodiacetic acid, glycolic acid, and formic acid as by-products was prepared from reagents. Glycine concentration was 11.1% by weight, concentrations of the by-products, namely, concentration of iminodiacetic acid, was 1.26% by weight, that of glycolic acid was 658 wtppm and that of formic acid was 321 wtppm, and amount of sodium ion was 21 wt ppm. 730 g of the resulting aqueous solution of crude glycine (pH =3.6) was passed, in the manner of down flow, through a resin column packed with 100 ml of a weakly basic anion exchange resin AMBERLITE IRA-96SB (trademark) of OH-form manufactured by Organo Co., Ltd. to obtain an aqueous glycine solution. The operation temperature was 40° C., and the liquid hourly space velocity of solution passing was 4.6 (L/L/Hr). The state of ion exchanging of iminodiacetic acid, which was an organic acid, was monitored in real time from the results of measuring the electric conductivity and pH of the treated solution at the outlet, and finally determined by OPA analysis. At the point of time when 650 ml of the aqueous solution was passed, pH=6.3 was observed, and it was confirmed that the solution was passed over the break through point of the weakly basic anion exchange resin, but the aqueous solution was further passed continuously, and when finally 700 ml of the aqueous solution was passed, the operation was terminated. By carrying out the OPA analysis after the experiment, it was found that leakage of iminodiacetic acid began from the point of time when 520 ml of the aqueous solution was passed. From this fact, it was found that passing of the aqueous solution of crude glycine over the break through point was carried out in an amount of 180 ml.

Thereafter, operation of forcing out of the residual aqueous solution of crude glycine with water was carried out in the manner of down flow by usual ion exchange operation. The operation temperature was 40° C., the liquid hourly space velocity of passing of the solution was 4.6 (L/L/Hr), and the passing amount was 100 ml. The state of replacement with water was confirmed from the results of measurement of electric conductivity of the treated solution at the outlet. Thereafter, back washing with water was carried out in the manner of upflow by usual ion exchange operation. The operation temperature was 25° C., the liquid hourly space velocity of passing was 4.6 (L/L/Hr), and the passing amount was 100 ml. Then, 1 N aqueous formic acid solution was allowed to contact with the weakly basic anion exchange resin to carry out ion exchanging with iminodiacetic acid trapped by the weakly basic anion exchange resin, and iminodiacetic acid was subjected to chromatographic separation to recover 96 ml of aqueous iminodiacetic acid solution. The operation temperature was 40° C., the liquid hourly space velocity of passing was 4.6 (L/L/Hr), and the passing amount was 200 ml. Thereafter, regeneration of the resin with 1 N aqueous sodium hydroxide solution in excess amount was carried out by usual ion exchange operation. The operation temperature was 40° C., the liquid hourly space velocity of solution passing was 4.6 (L/L/Hr), and the passing amount of the solution was 150 ml.

The state of ion exchanging was monitored in real time from the results of measuring the electric conductivity and pH of the treated solution at the outlet. The thus obtained aqueous glycine solution was subjected to the OPA analysis to confirm that the amount of glycine was 10.8% by weight and the iminodiacetic acid as a by-product was reduced to 167 wtppm/glycine group. According to the organic acid analysis, it was confirmed that glycol acid and formic acid as by-products were not detected. Furthermore, the concentration of iminodiacetic acid in the resulting aqueous iminodiacetic acid solution was 4.6% by weight, and that of glycine was less than 1 wtppm. The concentration of glycolic acid and that of formic acid were 802 wtppm and 119 wtppm, respectively. The recovery loss of glycine was 0.020% by weight. The recovery of iminodiacetic acid was 68% by weight.

COMPARATIVE EXAMPLE 3

Chromatographic separation of iminodiacetic acid with aqueous formic acid solution under such condition that the aqueous solution of crude glycine containing iminodiacetic acid, glycolic acid, and formic acid as by-products is not passed over the break through point:

In order to clarify the effect of passing the aqueous solution of crude glycine over the break through point, the operations of forcing out the residual aqueous glycine solution with water; back washing with water; chromatographic separation with 1 N aqueous formic acid solution; and regeneration with 1 N aqueous sodium hydroxide solution were successively carried out under the same conditions as in the examples, except that passing of the aqueous solution of crude glycine was stopped when the passing amount reached 520 ml, and the subsequent passing of the solution over the break through point was not carried out. As a result of analysis, the amount of ions of iminodiacetic acid in the resulting aqueous glycine solution was 187 wtppm/glycine group, and formic acid and glycolic acid were not detected. However, the amount of iminodiacetic acid in 98 ml of the resulting aqueous iminodiacetic acid solution was 4.5% by weight, and the glycine concentration was 3100 wtppm, and thus incorporation of glycine was recognized. The recovery loss of glycine was 0.38% by weight.

Next, Examples 4-8 and Comparative Examples 4-5 on the steps (3) and (4) will be explained.

The aqueous glycine solution treated in the steps (3) or (4) was one which was treated in the steps (1) and (2), but for convenience, here commercially available glycine α-crystal (and γ-crystal) were used as glycine sources.

EXAMPLE 4

Continuous Crystallization Experiment (1)

Ion-exchanged water was exclusively used as the water used in this experiment. The results of analysis on the components of this ion-exchanged water are shown in Table 5 together with the results of analysis of tap water used in Example 8. From the analytical values on Fe, Ca and Mg, the total amount of these cations was 0.11 μmol/L.

TABLE 5

| | Analytical values of water used in crystallization | | | |
|---|---|---|---|---|
| | Ion-exchange water | | Tap water | |
| | mg/L | μmol/L | mg/L | μmol/L |
| Fe | 0.0004 | 0.0072 | 0.0083 | 0.1486 |
| Chloride ion | 0.02 or less | | 27.0 | |
| Na | 0.0600 | 2.609 | 17.9 | 778.3 |
| Ca | 0.0030 | 0.075 | 22.0 | 548.9 |
| (as CaCO$_3$) | 0.0075 | | 55.0 | |
| Mg | 0.0006 | 0.025 | 5.3 | 218.1 |
| (as CaCO$_3$) | 0.0025 | | 21.8 | |
| Hardness (Ca + Mg) | 0.0100 | | 76.8 | |

6.4 kg of water was added to 3.6 kg of commercially available glycine α-crystal, and the mixture was introduced into a tank made of stainless steel, and the crystal was dissolved while heating to 90° C. to prepare a 36 wt % aqueous solution. A glass separable flask of 2 liters in internal volume equipped with a baffle, a jacket, and a double propeller blade of 70 mm in diameter was used as a crystallization cell. Warm water of 30° C. was circulated through the jacket. While stirring at 470 rpm, 1 liter of water was introduced into the crystallization cell. Thereafter, it was started to feed the 36 wt % aqueous solution of raw material glycine to the crystallization cell at a feed rate of 50 ml/min by a pump (namely, residence time of the raw material solution was 20 minutes). The temperature of warm water circulated through the jacket was controlled to keep the internal temperature of the crystallization cell at 40° C.

The tip of a nozzle connected to a tank, reduced in pressure by a vacuum pump, was introduced into the crystallization cell from the above, and the content of the cell was intermittently extracted so that the internal volume was kept at 1 liter. While this extraction operation was carried out at one time/2 minutes, the crystallization operation was continued. A slurry extracted after 2 hours from starting the experiment was filtered to obtain a cake. At this time, the slurry concentration was 12% by weight, and pH in the crystallization cell was 6.2 (39° C.). The resulting cake was vacuum dried at 40° C. for 2 hours to obtain a glycine crystal.

Figure 4:
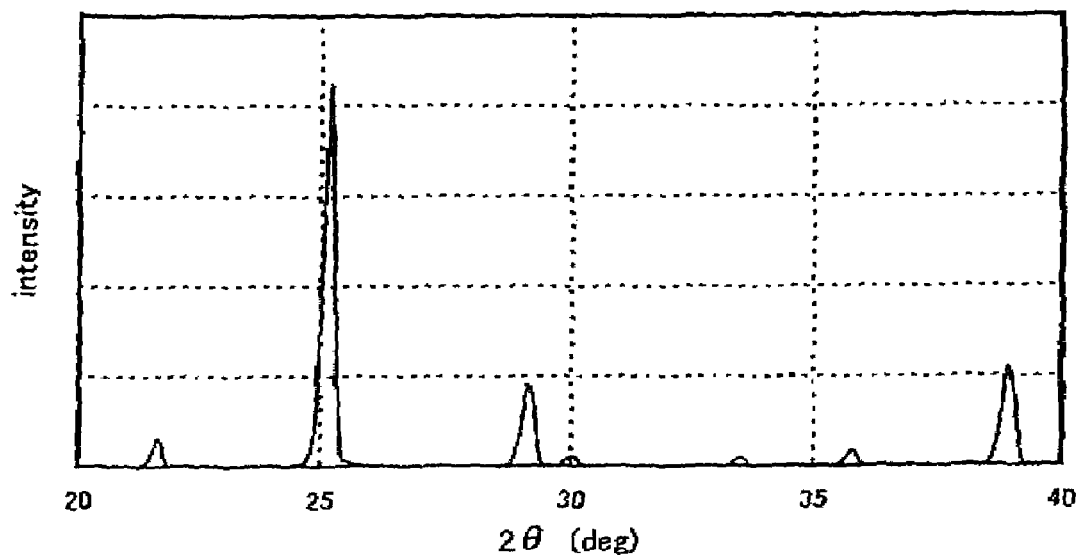
FIG. 4 shows results of measuring, according to X-ray diffractometry, the crystal obtained in Example 4.

With X-ray diffraction, the resulting glycine crystal was measured, and it was found that 100% of the crystal was γ-type glycine. The results of the measurement with X-ray diffraction are shown in FIG. 4. It is known that patterns of X-ray diffraction of α-type glycine and γ-type glycine have a characteristic peak at 2θ=29.8° in the case of α-type glycine and a characteristic peak at 2θ=25.2° in the case of γ-type glycine, as disclosed, for example, in WO01/02075. According to this example, it was found that even under such conditions as a residence time being 20 minutes, namely, degree of supersaturation being relatively high, the resulting crystal was γ-type glycine if crystallization was carried out using water containing substantially no multivalent cation.

EXAMPLE 5

Continuous Crystallization Experiment (2)

Figure 5:
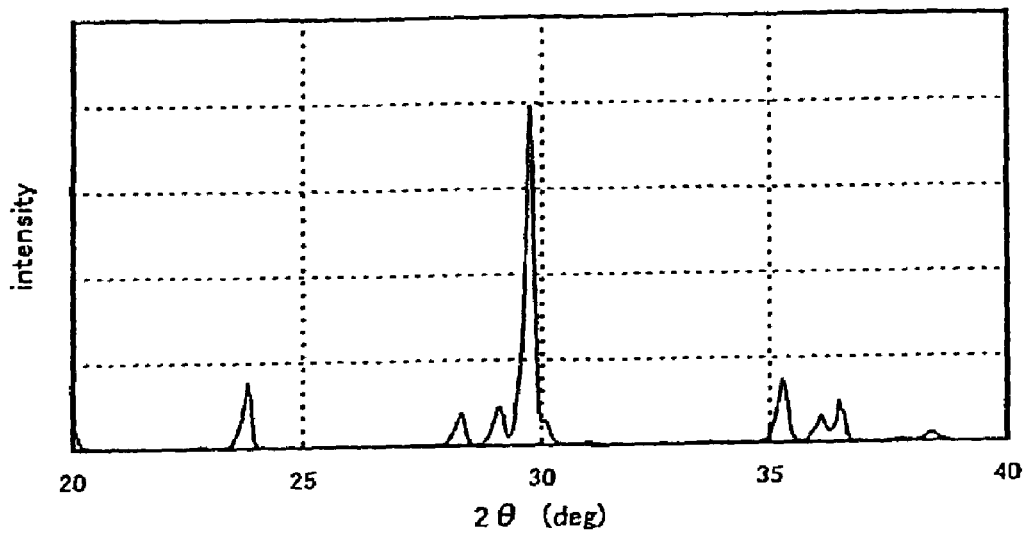
FIG. 5 shows results of measuring, according to X-ray diffractometry, the crystal obtained in Example 5.

25 mg of calcium carbonate was dissolved in 10 kg of the ion-exchanged water used in Example 4. That is, Ca concentration was 25 μmol/L. A crystallization experiment was conducted in the same manner as in Example 4, except that this water was used for the experiment. With X-ray diffraction, the resulting glycine crystal was measured, and it was found that 100% of the crystal was α-type glycine. Results of the measurement of the X-ray diffraction are shown in FIG. 5. According to this example, it was found that when crystallization was carried out using water containing 25 μmol/L of Ca as multivalent cation, the resulting crystal was α-type glycine.

EXAMPLE 6

Continuous Crystallization Experiment (3)

44 mg of zinc sulfate heptahydrate was dissolved in 10 kg of the ion-exchanged water used in Example 4. That is, Zn concentration was 15 μmol/L. A crystallization experiment was conducted in the same manner as in Example 4, except that this water was used for the experiment.

Measurement by X-ray diffraction of the resulting glycine crystal showed that 100% of the crystal was α-type glycine. According to this example, it was found that even when crystallization was carried out using water containing 15 μmol/L of Zn as multivalent cation, the resulting crystal was α-type glycine.

COMPARATIVE EXAMPLE 4

Continuous Crystallization Experiment (4):

0.5 g of sodium chloride was dissolved in 10kg of the ion-exchanged water used in Example 4. That is, Na concentration was 855 μmol/L. A crystallization experiment was conducted in the same manner as in Example 4, except that this water was used for the experiment.

A measurement, by X-ray diffraction, of the resulting glycine crystal showed that 100% of the crystal was γ-type glycine. According to this comparative example, it was found that even when crystallization was carried out using water containing 855 μmol/L of Na which was a monovalent cation, the resulting crystal was γ-type glycine as in the case of using ion-exchanged water, and monovalent cation such as Na was not a controlling factor for polymorphism of crystal.

COMPARATIVE EXAMPLE 5

Figure 6:
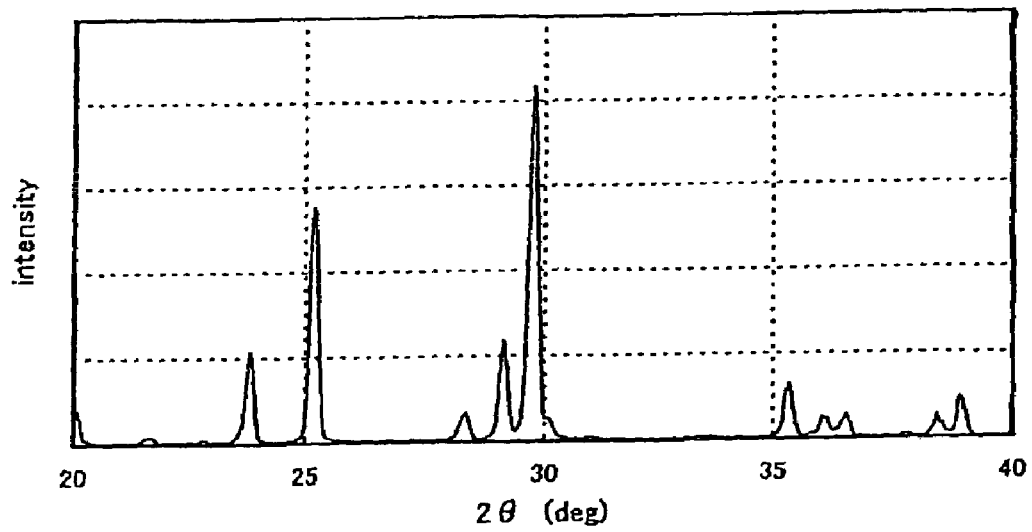
FIG. 6 shows results of measuring, according to X-ray diffractometry, the crystal obtained in Comparative Example 5.

Continuous Crystallization Experiment (5):

10 mg of calcium carbonate was dissolved in 10 kg of the ion-exchanged water used in Example 4. That is, Ca concentration was 10 μmol/L. A crystallization experiment was conducted in the same manner as in Example 4, except that this water was used for the experiment. A measurement by X-ray diffraction of the resulting glycine crystal showed that the glycine crystal was a mixed crystal of α-type glycine and γ-type glycine. Results of the measurement by X-ray diffraction are shown in FIG. 6. According to this comparative example, it was found that when crystallization was carried out using water containing a multivalent cation (Ca) in an amount of less than 15 μmol/L, α-type glycine could not stably be obtained.

EXAMPLE 7

Ion-exchanged water (results of analysis on its components are shown in Table 5) was exclusively used in this experiment. A glycine crystallization experiment was conducted using a crystallization cell of 50 L in internal volume. The crystallization cell was provided with a slow heating system using vacuum evaporation, a slurry circulating line, a slurry circulating pump, a jacket, a stirring blade of 240 mm in diameter, and a stirrer. The crystallization cell was a slurry circulating type, and a feeding port for a saturated aqueous solution of glycine, which was a raw material, was provided at the slurry circulating line.

Into a raw material tank made of stainless steel were introduced 72 kg of commercially available glycine α-crystal, 72 g of iminodiacetic acid, and 128 kg of ion-exchanged water, and dissolution was carried out by heating to 80° C. to prepare a 36 wt % aqueous solution of crude glycine. On the other hand, into a warm water tank were introduced 40 kg of glycine α-crystal and 126 kg of ion-exchanged water, and dissolution was carried out by heating to 50° C. to prepare a 24 wt % aqueous glycine solution.

The glycine solution was introduced into the crystallization cell from the warm water tank, the stirrer in the crystallization cell was set at 250 rpm, and the circulating pump was started. The slurry circulating flow rate was 1.5 m$^3$/Hr. The vacuum pump was started to gradually increase the degree of reduced pressure in the crystallization cell, and the temperature of the solution was reduced to 40° C. The apparatus was stopped, and 3 kg of commercially available γ-type glycine was added to the crystallization cell as a seed crystal. After termination of addition of the seed crystal, the stirrer, the vacuum pump, and the slurry circulating pump were started again.

Figure 7:
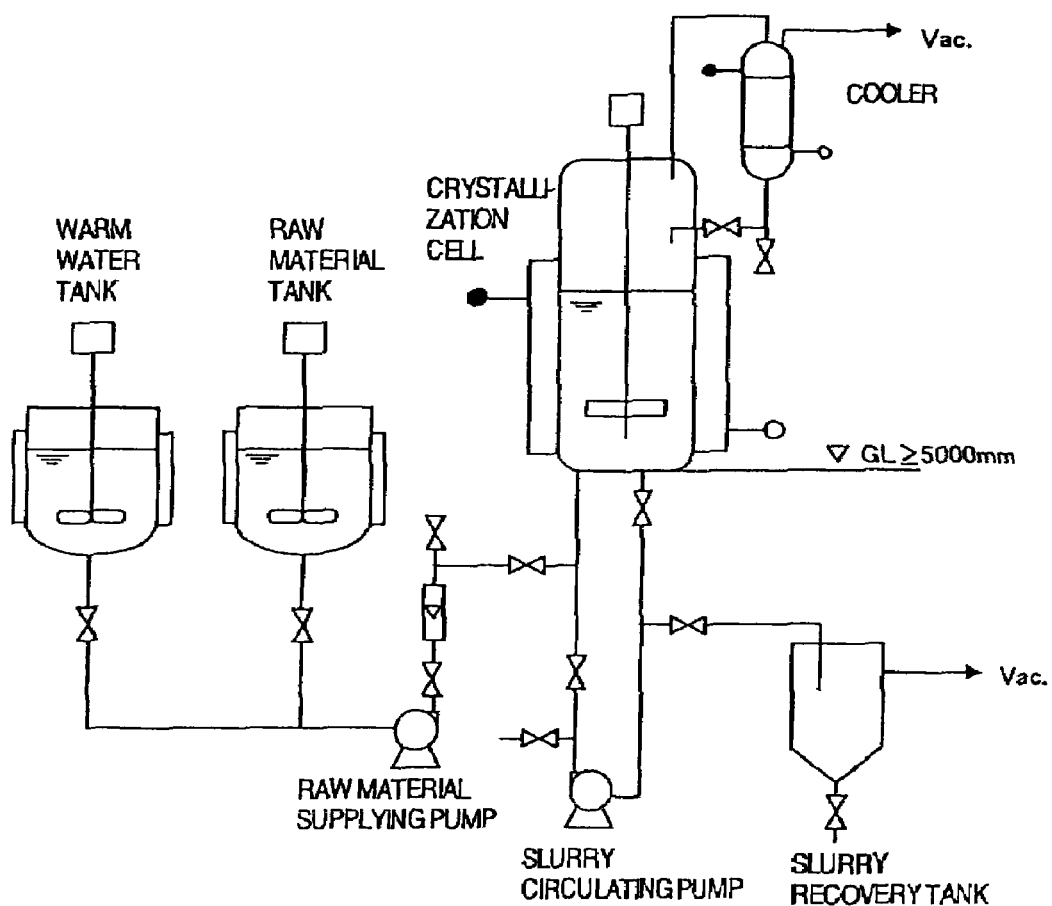
FIG. 7 shows the crystallization apparatus used in Example 7.

When the temperature in the crystallization cell was stabilized, the 36% aqueous solution of crude glycine kept at 80° C. was fed at a speed of 30 L/Hr from the raw material tank. The crystallization experiment was continued while recovering the slurry at intervals of 15 minutes so as to give a constant liquid level (30 L) in the crystallization cell. From the raw material feeding speed, the residence time was 1 hour. When 4 hours elapsed, the recovered slurry was separated into crystal and a mother liquor by a centrifugal separator to obtain a cake. At this time, the pH in the crystallization cell was 5.64. The resulting cake was vacuum dried at 40° C. for 2 hours to obtain glycine crystal. The apparatus of crystallization experiment is shown in FIG. 7.

Figure 8:
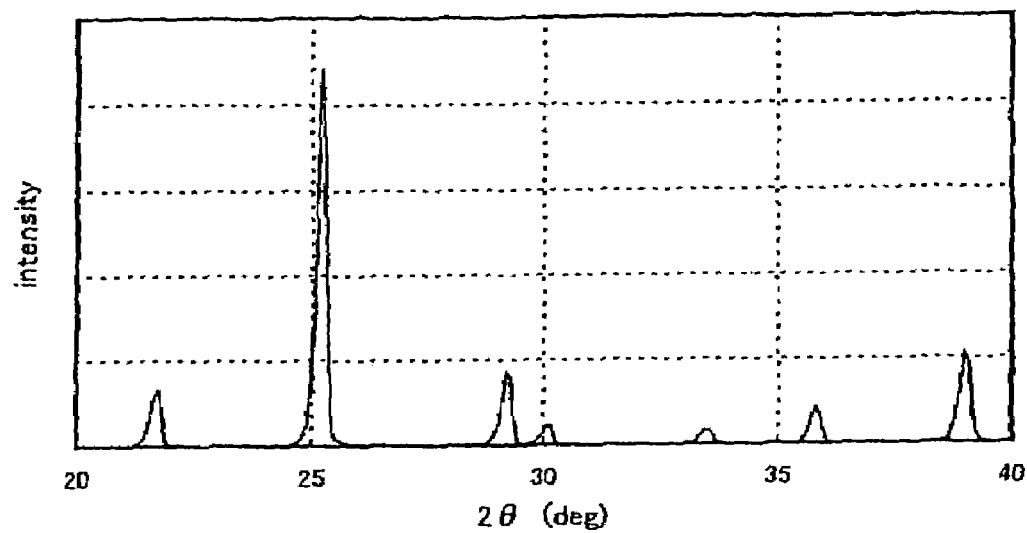
FIG. 8 shows results of measuring, according to X-ray diffractometry, the crystal obtained in Example 7.

A measurement of X-ray diffraction of the resulting glycine crystal showed that 100% of the crystal was γ-type glycine. Results of the measurement by X-ray diffraction are shown in FIG. 8. According to this example, it was found that when crystallization was carried out using water containing substantially no multivalent cation, the resulting crystal was γ-type glycine.

EXAMPLE 8

Figure 9:
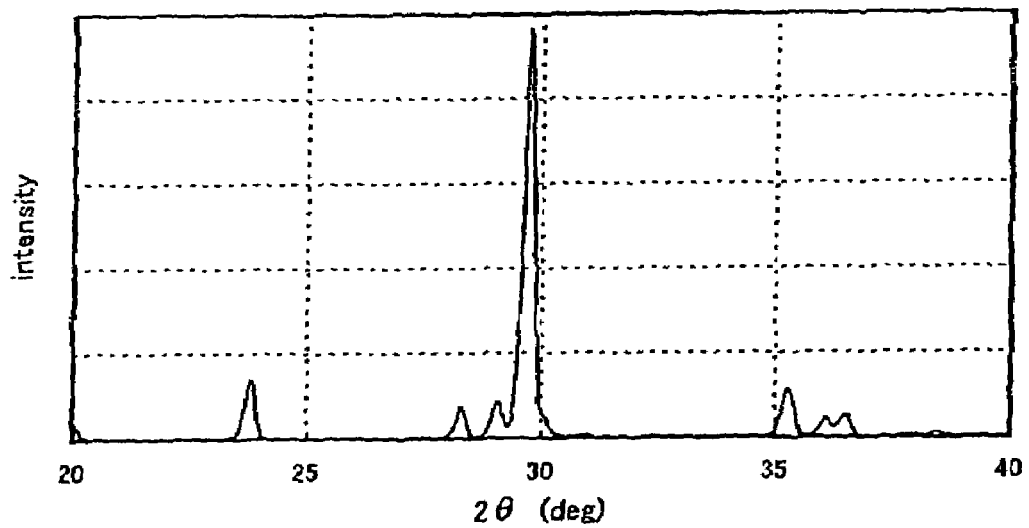
FIG. 9 shows results of measuring, according to X-ray diffractometry, the crystal obtained in Example 8.

A crystallization experiment was conducted in the same manner as in Example 7, except that tap water was used as water for the experiment (results of analysis on its components are shown in Table 5). A measurement by X-ray diffraction of the resulting glycine crystal showed that 100% of the crystal was α-type glycine. Results of the measurement by X-ray diffraction are shown in FIG. 9. According to this example, it was found that when crystallization experiment of Example 4 was carried out using tap water containing 550 μmol/L of Ca and 218 μmol/L of Mg as multivalent cations, the resulting crystal was α-type glycine even if a seed crystal of γ-crystal was inoculated.

INDUSTRIAL APPLICABILITY

The present invention provides an industrially useful method for producing or purifying amino acids, such as glycine, widely used as starting materials for food additives, medicines, agricultural chemicals, etc. Particularly, the present invention provides a method for purifying an amino acid from an alkali metal salt of amino acid synthesized by hydrolyzing reaction with an alkali metal and furthermore for simple separation and purification of iminodicarboxylic acid as a by-product and amino acid at high purity and high yield. The present invention further provides a method for simple crystallization of industrially useful α-type glycine and γ-type glycine at high purity.

The invention claimed is:
1. A method for purification of an amino acid from an aqueous solution of an alkali metal salt of the amino acid, comprising:
   (1) cation exchanging, which comprises subjecting the aqueous solution of the alkali metal salt of amino acid to a desalting purification treatment using a cation exchange resin to obtain an aqueous solution of a crude amino acid, wherein said cation exchanging is carried out using a moving bed type continuous ion exchange apparatus; and
   (2) anion exchanging, which comprises adsorbing an iminodicarboxylic acid using a weakly basic anion exchange resin, the iminodicarboxylic acid being a coexisting by-product produced together with the crude amino acid, to remove the iminodicarboxylic acid from the resulting aqueous solution of the crude amino acid, wherein the aqueous solution of the crude amino acid is passed over the weakly basic anion exchange resin even after the iminodicarboxylic acid has reached the break through point at which the weakly basic anion exchange resin leaks the iminodicarboxylic acid, such that anion exchanging occurs between the iminodicarboxylic acid and the crude amino acid, thereby recovering any amino acid adsorbed to the weakly basic anion exchange resin.

2. A method according to claim 1, wherein the step (2) comprises a series of the following steps for recovering amino acid from the aqueous solution of crude amino acid containing iminodicarboxylic acid:
   a) contacting the aqueous solution of crude amino acid containing iminodicarboxylic acid with a weakly basic anion exchange resin to subject the by-product iminodicarboxylic acid to ion exchanging, thereby producing an aqueous solution of amino acid;
   b) further consecutively contacting the aqueous solution of crude amino acid containing iminodicarboxylic acid with the weakly basic anion exchange resin even after adsorbing the iminodicarboxylic acid to the break through point of the weakly basic anion exchange resin, thereby ion exchanging the amino acid trapped by the weakly basic anion exchange resin with iminodicarboxylic acid to recover amino acid,
   c) forcing out and washing with water the aqueous solution containing amino acid which remains in the weakly basic anion exchange resin,
   d) passing water from the bottom part of the weakly basic anion exchange resin to carry out back washing,
   e) regenerating the weakly basic anion exchange resin by contacting an aqueous solution of alkali metal hydroxide with the weakly basic anion exchange resin, and
   f) forcing out and washing with water the aqueous solution containing alkali metal salt of iminodicarboxylic acid which remains in the weakly basic anion exchange resin.

3. A method according to claim 1, wherein the amino acid comprises at least one amino acid selected from the group consisting of glycine, alanine, and methionine.

4. A method according to claim 1, wherein the cation exchange resin used in the step (1) is a weakly acidic cation exchange resin.

5. A method according to claim 1, wherein the moving bed type continuous ion exchange apparatus used in the step (1) comprises at least three columns of 1: an exchange column which carries out ion exchange reaction, 2: a replacing column which replaces the solution carried by the ion exchange resin, and 3: a regeneration column which regenerates the resin exchanged with alkali metal ions to an H-form resin with an aqueous solution of mineral acid supplied.

6. A method according to claim 1, wherein the iminodicarboxylic acid comprises at least one acid selected from the group consisting of iminodiacetic acid, iminodipropionic acid, and iminodi-4-methylthiobutyric acid.

7. A method according to claim 3, wherein the amino acid comprises glycine.

8. A method according to claim 7, wherein the combination of amino acid and iminodicarboxylic acid is a combination of glycine and iminodiacetic acid and the aqueous solution of crude amino acid contains glycolic acid and/or formic acid in addition to iminodiacetic acid as by-products.

9. A method according to claim 7 further comprising the step (3): purifying glycine by crystallizing only γ-type glycine from the aqueous solution containing glycine which has been subjected to the steps (1) and (2), wherein water containing no multivalent cation is used as a solvent for crystallization.

10. A method according to claim 7, further comprising the step (4): purifying glycine by crystallizing only α-type glycine from the aqueous solution containing glycine which has been subjected to the steps (1) and (2), wherein water containing at least one kind of multivalent cation in an amount of at least 15 µmol/L is used as a solvent for crystallization.

11. A method according to claim 2, wherein the amino acid comprises at least one amino acid selected from the group consisting of glycine, alanine, and methionine.

12. A method according to claim 2, wherein the cation exchange resin used in the step (1) is a weakly acidic cation exchange resin.

13. A method according to claim 2, wherein the moving bed type continuous ion exchange apparatus used in the step (1) comprises at least three columns of 1: an exchange column which carries out ion exchange reaction, 2: a replacing column which replaces the solution carried by the ion exchange resin, and 3: a regeneration column which regenerates the resin exchanged with alkali metal ions to an H-form resin with an aqueous solution of mineral acid supplied.

14. A method according to claim 2, wherein the iminodicarboxylic acid comprises at least one acid selected from the group consisting of iminodiacetic acid, iminodipropionic acid, and iminodi-4-methylthiobutyric acid.

15. A method according to claim 11, wherein the amino acid comprises glycine.

16. A method according to claim 15, wherein the combination of amino acid and iminodicarboxylic acid is a combination of glycine and iminodiacetic acid and the aqueous solution of crude amino acid contains glycolic acid and/or formic acid in addition to iminodiacetic acid as by-products.

17. A method according to claim 16 further comprising the step (3): purifying glycine by crystallizing only γ-type glycine from the aqueous solution containing glycine which has been subjected to the steps (1) and (2), wherein water containing no multivalent cation is used as a solvent for crystallization.

18. A method according to claim 16, further comprising the step (4): purifying glycine by crystallizing only α-type glycine from the aqueous solution containing glycine which has been subjected to the steps (1) and (2), wherein water containing at least one kind of multivalent cation in an amount of at least 15 µmol/L is used as a solvent for crystallization.

* * * * *